(12) United States Patent
Zurn

(10) Patent No.: US 9,049,988 B2
(45) Date of Patent: Jun. 9, 2015

(54) AUTOMATED VESSEL REPAIR SYSTEM, DEVICES AND METHODS

(76) Inventor: William Harrison Zurn, Sunnyvale, CA (US)

( * ) Notice: Subject to any disclaimer, the term of this patent is extended or adjusted under 35 U.S.C. 154(b) by 1090 days.

(21) Appl. No.: 12/912,383

(22) Filed: Oct. 26, 2010

(65) Prior Publication Data

US 2011/0040177 A1 Feb. 17, 2011

Related U.S. Application Data

(62) Division of application No. 11/895,681, filed on Aug. 27, 2007, now Pat. No. 7,979,108.

(51) Int. Cl.
  *A61B 5/05* (2006.01)
  *A61B 5/00* (2006.01)
  *G01R 33/28* (2006.01)
  *G01R 33/48* (2006.01)

(52) U.S. Cl.
  CPC ............... *A61B 5/0031* (2013.01); *A61B 5/411* (2013.01); *G01R 33/285* (2013.01); *G01R 33/4812* (2013.01)

(58) Field of Classification Search
  CPC .......... A61B 5/01; A61B 5/0008; A61B 8/00; A61B 8/4888
  USPC ........... 600/407, 409–410, 427; 324/306, 308
  See application file for complete search history.

(56) References Cited

U.S. PATENT DOCUMENTS

| | | | |
|---|---|---|---|
| 3,657,744 A | 4/1972 | Ersek | |
| 4,061,134 A | 12/1977 | Samuels et al. | |
| 4,140,126 A | 2/1979 | Choudhury | |
| 4,276,874 A | 7/1981 | Wolvek et al. | |
| 4,560,374 A | 12/1985 | Hammerslag | |
| 4,617,932 A | 10/1986 | Kornberg | |
| 4,655,771 A | 4/1987 | Wallsten | |
| 4,728,328 A | 3/1988 | Hughes et al. | |
| 4,732,152 A | 3/1988 | Wallsten et al. | |
| 4,739,762 A | 4/1988 | Palmaz | |
| 4,787,899 A | 11/1988 | Lazarus | |
| 4,795,458 A | 1/1989 | Regan | |
| 4,830,003 A | 5/1989 | Wolff et al. | |
| 4,892,539 A | 1/1990 | Koch | |
| 4,913,141 A | 4/1990 | Hillstead | |
| 4,954,126 A | 9/1990 | Wallsten | |
| 4,969,896 A | 11/1990 | Shors | |
| 4,994,071 A | 2/1991 | MacGregor | |
| 4,998,539 A | 3/1991 | Delsanti et al. | |
| 5,024,671 A | 6/1991 | Tu | |
| 5,026,377 A | 6/1991 | Burton et al. | |
| 5,035,706 A | 7/1991 | Giantureo et al. | |

(Continued)

OTHER PUBLICATIONS

Timothy F Kirn, Endovascular AAA Repair is Gaining. Expert Asserts, VascularWeb, Provided by the Society for Vascular Surgery, vol. 1—2005 Issue 2.

(Continued)

*Primary Examiner* — Joel F Brutus
(74) *Attorney, Agent, or Firm* — Alan W. Cannon; Law Office of Alan W. Cannon

(57) ABSTRACT

Systems, devices and automated methods for minimally invasive surgery. A device is fabricated of bio-compatible semiconductor elements, and can be assembled, delivered, navigated and implanted by automated methods, using Nuclear Magnetic Resonance (NMR) technology.

13 Claims, 8 Drawing Sheets

(56) References Cited

U.S. PATENT DOCUMENTS

| | | | |
|---|---|---|---|
| 5,047,050 A | 9/1991 | Arpesani | |
| 5,078,726 A | 1/1992 | Kreamer | |
| 5,084,065 A | 1/1992 | Weldon | |
| 5,090,959 A | 2/1992 | Samson et al. | |
| 5,102,417 A | 4/1992 | Palmaz | |
| 5,104,399 A | 4/1992 | Lazarus | |
| 5,104,404 A | 4/1992 | Wolff | |
| 5,122,154 A | 6/1992 | Rhodes | |
| 5,123,917 A | 6/1992 | Lee | |
| 5,158,548 A | 10/1992 | Lau | |
| 5,192,297 A | 3/1993 | Hull | |
| 5,201,757 A | 4/1993 | Heyn et al. | |
| 5,207,695 A | 5/1993 | Trout, III | |
| 5,219,355 A | 6/1993 | Parodi et al. | |
| 5,275,622 A | 1/1994 | Lazarus et al. | |
| 5,282,824 A | 2/1994 | Gianturco | |
| 5,316,023 A | 5/1994 | Palmaz et al. | |
| 5,360,443 A | 11/1994 | Barong et al. | |
| 5,395,334 A | 3/1995 | Keith et al. | |
| 5,397,345 A | 3/1995 | Lazarus | |
| 5,489,295 A | 2/1996 | Piplani et al. | |
| 5,562,728 A | 10/1996 | Lazarus | |
| 5,609,625 A | 3/1997 | Piplani | |
| 5,628,783 A | 5/1997 | Quiachon | |
| 5,662,700 A | 9/1997 | Lazarus | |
| 5,669,936 A | 9/1997 | Lazarus | |
| 5,776,111 A * | 7/1998 | Tesio | 604/264 |
| 5,824,015 A * | 10/1998 | Sawyer | 606/214 |
| 5,830,209 A | 11/1998 | Savage et al. | |
| 5,951,566 A * | 9/1999 | Lev | 606/108 |
| 6,004,269 A | 12/1999 | Crowley et al. | |
| 6,019,784 A | 2/2000 | Hines | |
| 6,027,863 A | 2/2000 | Donadio, III | |
| 6,033,398 A | 3/2000 | Farley et al. | |
| 6,074,374 A | 6/2000 | Fulton | |
| 6,107,004 A | 8/2000 | Donadio, III | |
| 6,139,511 A | 10/2000 | Huter et al. | |
| 6,146,814 A | 11/2000 | Millet | |
| 6,203,732 B1 | 3/2001 | Clubb et al. | |
| 6,210,362 B1 | 4/2001 | Ponzi | |
| 6,251,128 B1 | 6/2001 | Knopp et al. | |
| 6,272,370 B1 * | 8/2001 | Gillies et al. | 600/411 |
| 6,374,476 B1 | 4/2002 | Ponzi et al. | |
| 6,375,606 B1 * | 4/2002 | Garibaldi et al. | 600/12 |
| 6,463,317 B1 * | 10/2002 | Kucharczyk et al. | 600/411 |
| 6,520,934 B1 | 2/2003 | Lee et al. | |
| 6,524,303 B1 | 2/2003 | Garibaldi | |
| 6,673,104 B2 | 1/2004 | Barry | |
| 6,696,335 B2 | 2/2004 | Bonart | |
| 6,980,843 B2 | 12/2005 | Eng et al. | |
| 6,998,358 B2 | 2/2006 | French et al. | |
| 7,242,301 B2 | 7/2007 | August et al. | |
| 2002/0133219 A1 | 9/2002 | Barry | |
| 2003/0065355 A1 * | 4/2003 | Weber | 606/200 |
| 2005/0159802 A1 | 7/2005 | Furst et al. | |
| 2005/0182319 A1 * | 8/2005 | Glossop | 600/424 |
| 2006/0232417 A1 | 10/2006 | August et al. | |
| 2006/0287595 A1 * | 12/2006 | Maschke | 600/424 |
| 2008/0004595 A1 | 1/2008 | Viswangthan et al. | |
| 2008/0262593 A1 * | 10/2008 | Ryan et al. | 623/1.12 |

OTHER PUBLICATIONS

Karen M. Dente, M.D., Endovascular Repair for Aneurysm Rupture, VascualrWeb, Provided by the Society for Vascular Surgery, vol. 2—2006 Issue 1.

Hank Russell, Imaging System Tested for Visualizing Stents, VascularWeb, Provided by the Society for Vascular Surgery, vol. 2—2006 Issue 1.

Hank Russell, CT Angiography Shows Promise in Arterial Imaging, VasculaWeb, Provided by the Society for Vascular Surgery, vol. 2—2006 Issue 1.

Jane Salodof Macneil, Stenting or Open Repair? EVAR, DREAM Trials Inconclusive, VascularWeb, Provided by the Society for Vascular Surgery, vol. 2—2006 Issue 1.

Frank J. Veith, M.D., The Rush to Stent: A Cause for Concern, VascularWeb, Provided by the Society for Vascular Surgery, vol. 2—2006 Issue 2.

Mark S. Lesney, Aortic Debranching Can Aid Endovascular Repair of TAA, VascularWeb, Provided by the Society for Vascular Surgery, vol. 2—2006 Issue 2.

Y. Joseph Woo, MD, Acute Aortic Dissection: A Case for Specialized Centers Colleague Company Commentary, VascularWeb, Provided by the Society for Vascular Surgery, vol. 2—2006 Issue 3.

Jeff Evans, AAA Repair: Early Intervention or Wait and See?, VascularWeb.Provided by the Society for Vascular Surgery, vol. 2—2006 Issue 3.

Timothy F. Kim, Endovascular Emergency Repair of Ruptured AAA Uses Balloon Technique, Vascular Web.Provided by the Society for Vascular Surgery, vol. 2—2006 Issue 3.

Timothy F. Kim, Endovascular Aortic Repair Less Harmful to Heart?, VascularWeb.Provided by the Society for Vascular Surgery, vol. 2—2006 Issue 3.

Timothy F. Kim, European Series: Carotid Stent vs. Endarterectomy, VascularWeb,Provided by the Society for Vascular Surgery, vol. 2—2006 Issue 3.

Frank J. Criado, MD, Ronald M. Fairman, MD, and Gary J. Becker, MD, Taletn LPS AAA stent graft: Results of a pivotal clinical trial, Journal of Vasculr Surgery vol. 37, No. 4 , 2006.

Zimmermann, Michael M.D., Ph.D.; Krishnan. René M.D.; Raabe, Andreas M.D., Ph.D.; Seifert, Volker M.D., Ph.D., Robot-assisted Navigated Neuroendoscopy, Neurosurgery: vol. 51(6) Dec. 2002 pp. 1446-1452.

John Carey, No One Wanted to Hear, Business Week, Oct. 9, 2006, pp. 91-92.

Andrew Bridges, FDA: Stent Patients Face Blood Clot Risk, Associated Press, Dec. 5, pp. 1-3, 2006.

Andrew Bridges, FDA: Heart Stents Don't Up Risk of Death. Associated Press, Dec. 7, 2006.

A. Kastalsky, et al., Semiconductor high-energy radiation scintillation detector, pp. 650-656, 2006.

Timothy J. Parker, Pixellated NaI(T1). For Enhanced Performance 2001, 2 pgs.

CAT Scan (CT)—Body, download Mar. 19, 2009, pp. 1-6. http://www.radiologyinfo.org/en/info.cfm?PG=bodyct.

http://universe-review.ca/I08-24-scintillator.jpg.

http://images.search.yahoo.com/search/images/view?frame=top&back=http%3A%2F%F%2Fs . . . .

http://www.upei.ca/~phys221/MH/How_they_work_/how_they_work_.html.

\* cited by examiner

AUTOMATED VESSEL REPAIR SYSTEM, DEVICES AND METHODS

CROSS REFERENCE

This application is a divisional application of application Ser. No. 11/895,681, filed Aug. 27, 2007, which is incorporated herein by reference in its entirety and to which application we claim priority under 35 USC §120.

FIELD OF THE INVENTION

The field of the invention relates to medical devices. More particularly, the present invention relates to endovascular placement of grafts within a patient.

BACKGROUND OF THE INVENTION

Because the aorta is the main artery carrying blood from the heart to the rest of the body, an aneurysm in this artery, called an aortic aneurysm, is especially serious. The bursting of this main artery can be fatal unless it's treated immediately. An aortic aneurysm larger than about 4 cm. in diameter in this section of the aorta is ominous. Left untreated, the aneurysm may rupture, resulting in rapid, and usually fatal, hemorrhaging.

For reconstruction of essential vessels such as the aorta, surgical restoration is extremely life-threatening. Surgical methods entail significant surgery in which an artificial section of vessel is implanted into the diseased or impeded lumen. The weak portion of the lumen may be surgically separated and an artificial graft stitched to the ends of the vessel.

Other devices for the repair of vessels such as arteries include a NITINOL® coil with a graft. The NITINOL® coil is diminished in proportion as it cools. When arranged in the body, its temperature increases, and it returns to a preferred dimension to clamp a graft within the lumen of the vessel. These devices are detailed in Charles T. Dottner, et al., Transluminal Expandable Nitinol Coil Stent Grafting: Preliminary Report, Radiology 147:259-260, April 1983, and Andrew Cragg, et al., Nonsurgical Placement of Arterial Endoprostheses: A New Technique Using Nitinol Wire, Radiology 147:261-263, April 1983.

While some aneurysms cause no noticeable symptoms, others cause chest or back pain. Often an aneurysm first shows up on a chest X-ray. The stent and location of the aneurysm can be estimated through echocardiography or through radiological imaging—either magnetic resonance imaging (MRI) or computed tomography (CAT or CT) scanning. Patients who are found to have small aneurysms can be monitored and examined regularly, but those with large or dissecting ones need prompt treatment, because the rupture of an aneurysm can be fatal.

Description of the prior art includes such devices as intravascular devices, called "stents", which are placed in the organism by means of mechanical placement on balloons or other types of catheters. Catheters are a type of tubular metal or rubber instrument designed to pass through canals such as arteries.

The accepted surgical technique of eradicating the aneurysm and replacing the weakened area with a prosthetic graft has been continuously improved over the years.

The use of prior art still causes a relatively high mortality rate for patients undergoing the surgery. One reason for the high fatality rate is that the procedure constitutes a major surgical endeavor, making it highly elective in patients with severe coronary or cerebral arteriosclerosis, severe confining pulmonary disease, consequential renal disease or other complicating factors. Consequently, even though particular techniques have been advanced recently that elude or reduce the stress, morbidity, and risk of mortality associated with surgical intervention to repair aortic aneurysms, the methods that have been perfected do not effectively treat the aneurysm. These methods also do not eliminate the influenced section of aorta from the pressures and stresses associated with the circulation. The devices disclosed in the prior art do not furnish a reliable and quick means to bypass an aneurysmal artery.

Prior art also relates to prostheses consisting of two attachment means, or stents, connected by means of a flexible coaxial tube, which is implanted along the arterial zone influenced by the aneurysm. The ideal material used for stents should include fundamentally the following characteristics: it should not have any toxic, allergic or carcinogenic action, and should be pathologically inert. The stent should be tolerated by the organism: it should have an elevated degree of elasticity. It should also allow host fibroblasts to pierce the thickness of the prosthesis wall by adhering to the surrounding tissues.

Correspondingly, inside the vessel channel, the cells coming from the blood can adhere to the surface and arrange a layer defined as neointima. Furthermore, it is necessary that the prosthesis material can be submitted to the various sterilization procedures without losing its properties and can be easily shaped. Occasionally, the prosthesis detaches in the suture, thus causing the formation of scar tissue that, by collapsing due to the blood pressure, causes a pseudoaneurysm, which in turn, causes the prosthesis end to come off the artery end to which it was associated. Vascular prostheses have been used to accomplish bypass operations and to repair damaged vessels in the body such as arteries and veins.

Often, a piece of one's own vessel is taken from another part of the body to form the prosthesis. This involves putting the patient through an additional surgical operation. In addition, in many patients, suitable vessels are not available.

In one type of pathology, a layer of expanded scar tissue forms around the prosthesis; thereby the arterial blood laminar flow becomes vertical which produces thrombi stratification within the scar tissue.

These stents, used as a means of attachment for intravascular prostheses, can be deformed by enlarging their diameter when subjected to enlargement from inside by inflation of a balloon, until they are restrained against the internal side of the arterial wall. An alternative method of delivery properties to the body which have a tendency to take a radially enlarged position is to attach the elements to each other at the points of crossing in a suitable manner, for example, by some form of welding, gluing or similar occurrence.

With the current balloon catheter devices, the attachment of stents on ends of the prosthesis is an exhausting, dangerous and time-consuming procedure. Prior art includes using the femoral artery to insert these rigid and cumbersome intra-aortic balloon catheters because of the large diameter of that artery. Nonetheless, substantial surgery must be performed in order to reach and isolate the femoral artery.

In addition, a large incision must be made in the femoral artery wall to allow introduction of these prior art devices. The safety of intra-aortic balloon pumping using the catheters of the prior art has been controversial since they can bring about, and in some instances have caused, aortic dissections, punctures and trauma chiefly because of the proportionate stiffness of the devices.

Furthermore, this stiffness prevents precise maneuverability of the catheter within the vascular shape and consequently restricts its chances of effectiveness. It is acknowledged in the prior art that insertion and controlling of catheters is complicated and that trauma and injury to the incision and blood vessel may occur during the insertion and controlling of the catheter.

The technique of the introduction of catheters with inflatable balloons is known as valvuloplasty and angioplasty treatments, in which dilation catheters for one or more lumina are used. If it is desired to implant a prosthesis of a type mentioned above with the current dilation catheters, the catheters consist of two attachment means or stents. The stents are coaxially connected together by means of a flexible tube. It is necessary to use two catheters, one at a time, to consecutively dilate the proximal stent and the distal stent. This maneuver is difficult, risky and time-consuming, and is not recommended.

Prior art also includes a method of repairing arteries, which involves inserting the stent device (stainless steel wire about 0.018 in.) through the groin, and using it to patch the aneurysm. This was determined a significant proposition and would exclude the need for more invasive and risky surgery inside the abdomen. The suffering and jeopardy to life ordinarily associated with aortic aneurysms demands surgical remedy in a preponderance of situations. Prior art also includes methods of using devices for the repair of lumens such as blood vessels and arteries by use of a NITINOL® (nickel-titanium alloy) coil with a graft. The NITINOL® coil is reduced in dimension as it cools and then the coil is heated to change its dimensions. Ordinarily acknowledged manners of execution can be the basis of consequential trauma to the patient.

Also, existing methods allow a grafting system that provides catheter-based delivery and implantation of a specialized, sutureless prosthesis to repair abdominal aortic aneurysms. The prior art procedure is traumatic to the patient, often causes major surgery, and may be dangerous or impossible to perform if, as is not infrequent, the health of the patient is poor.

Aneurysm surgery has been performed for approximately fifty years. The accepted surgical procedure of eradicating the aneurysm and replacing the weak artery or vein surface with a prosthetic graft has been constantly refined. Even so, the fatality rate for patients enduring the surgery is still seriously elevated. One reason for the high fatality rate is that the procedure presents a significant surgical endeavor, making it enormously discretionary in patients with severe coronary or cerebral arteriosclerosis.

The two most widely used approaches are resection of the aneurysm or the performing of an axillobifemoral bypass occurring with the coagulated process of the aneurysm repair.

The axillobifemoral bypass method leaves the aneurysm open at the proximal end. The danger of this procedure is that the clot of an infra-renal aneurysm may propagate over the renal arteries causing loss of blood flow to the kidneys and possibly resulting in renal failure.

Additionally, the grafted artery placed during the procedure is adjacent the exterior of the skin where it is receptive to injury. The considerable rerouting completed by the bypass may also cause complications. Present treatments are considerably invasive; many times a patient consequently expires during the repair operation.

The resection method requires a large surgical opening into the abdominal cavity with surgical penetration of a prosthetic graft inside the flawed segment. The surgical invasion of the abdominal cavity greatly increases the complications and mortality of procedure, especially with respect to the majority of those patients with such aneurysms that also exhibit other reasons for hospitalization.

Another major disadvantage of presently accepted eradication aneurysm surgical techniques is that because of the severe nature of the operation, it can be performed only in sophisticated medical centers having the potential to carry out superior cardiovascular surgery. If the prognosis is not made until the diagnosis for a rupture is determined, mortality has been known to occur because of the unsatisfactory amount of time to transfer the patient to a major medical center where remedial operation could be discharged.

Choudhury (e.g., see U.S. Pat. No. 4,140,126) proposed a less invasive surgical procedure. This method comprises a procedure for restoring an aortic aneurysm using a catheter inserted into the femoral artery and transferred to the site of the aneurysm. The only incision required is proportionately small and is fashioned in the leg of the patient. The catheter maintains a pair of expanding rings spaced barely more than the length of the aneurysm. Many mooring pins, which extend radically of the catheter, are attached to the rings.

The prosthetic graft is held by the mooring pins in a collapsed position smaller than the inside diameter of the artery. Once inserted, the rings are enlarged and the anchoring pins pierce the aortic walls, holding the graft in place with the help of the hemodynamic pressure of blood in the aorta.

The Choudhury method, while much less invasive than the generally accepted surgical techniques, has several particular drawbacks. The anchoring pins used to hold the graft in place, first on the catheter and then in the aorta, pierce the aortic wall and may cause consequential impairment to the aorta, particularly near the region of the aneurysm that has already seriously weakened the aorta. The pins do not reliably grip the graft in location within the walls of the aorta. The procedure also is completed while blood continues flowing through the aorta, the aneurysm site, and the femoral artery. The graft of Choudhury expands only a very small distance below the site of the aneurysm; consequently, the area of healthy vessel to which it must become attached is very small, resulting in drainage around the graft or the graft not sticking to the vessel.

Many ruptures have been reported to the FDA worldwide among the roughly 13,500 patients treated with the presently used stent graft. Other problems include: poor placement of the graft, leakage (endoleak), movement or migration of the device after it is implanted and metal frame fractures in the device, suture and fabric tears.

Accordingly, there is a need in the art for less invasive repair procedures for repairing aneurysms and other defects in arteries such as the aorta or other arteries or vessels. There is a continuing need for methods, systems and devices for executing an aneurysm repair, which does not require major surgery and which may be used on higher risk patients than what conventional aneurysm surgery currently allows.

SUMMARY OF THE INVENTION

A method of implanting a device in a vessel or duct of a patient is provided, including the steps of: scanning the patient to provide a map of a target surgical location of a defect in the vessel or duct; programming coordinates of the target surgical location relative to the map in a computer controller; inserting the device through a small opening in the patient; moving and guiding the device through the anatomy of the patient to the target location, wherein guiding is performed by registering the device mover with the map to provide precise navigation of the device through the anatomy and to the target surgical location; and fixing the device to the target surgical location.

A minimally invasive method of implanting a device in a patient is provided, including the steps of: scanning the patient to provide a map of a target surgical location in the patient; programming coordinates of the target surgical location relative to the map in a computer controller; inserting the device through a small opening in the patient; moving and guiding the device through the anatomy of the patient to the target location, wherein guiding is performed by registering the device mover with the map to provide precise navigation of the device through the anatomy and to the target surgical location; and fixing the device to the target surgical location.

An implantable device is provided that includes a plurality of cells interconnected by magnetic attraction forces.

A biocompatible semiconductor cell usable to assemble an implant device is provided, including: a communication element configured to receive radio frequency energy from a source external of the cell; polarity regions adjacent edges of the cell; and a communication link between the communication element and each of the polarity regions, wherein radio frequency energy received by the communication element is transmittable via the communication links to alter polarity of one or more of the polarity regions.

One of the purposes of the invention is, along with other aspects, to repair weak arteries, vein walls, or other human body vessels. Repairing weak artery walls can prevent aneurysms. An aneurysm is the bulging out of the wall of a weakened blood vessel. If the bulging becomes extreme and stretches the vessel wall beyond its limit, the vessel may rupture. Various types of aneurysms or other degenerate diseases may influence the capability of the human vessels to conduct fluids and in turn may be life threatening.

The present invention overcomes prior art shortcomings by use of semiconductor manufacturing methodology, such as, nano manufacturing techniques to produce an internal prosthesis (stent). After producing the stent, the invention allows the detection of the stent (prosthesis), and controlling, positioning and fusing to the vessel wall by means of a Nuclear Magnetic Resonance (NMR) control system. Accordingly, a device that allows the detection, control and positioning within the vessel in need of repair is provided.

In at least one embodiment, a device is provided that is mobile from a collapsed (strong polarity) configuration of an expanse less than the diameter of the vessel to an expanded state (weak polarity). The expanded state is an open fabrication of a diameter more or less equal to that of the vessel wall (or slightly greater) in need of repair. The collapsed state provides a condition that is useful to reduce its radial dimension without producing oblique or transverse folds and/or wrinkles.

Devices according to the present invention can be used in many medical applications. As mentioned, these devices may be employed in miscellaneous types of aneurysm prevention reflected by some form of vessel widening, or the opposite, stenosis, which involves contraction of blood vessels. The invention can be used to sustain and keep open vessels of venous systems, to close pathological vessel deficiency. The invention can also be used to bridge pathological vessel dilatations and ruptures in interior vessel walls or to brace bronchial tubes and bronchi.

Devices according to the present invention are made of material tolerated by the human body, and can be applied within, or replace part of, for example, blood vessels in the body of a living animal, a living human or some other intricate accessible place within either. Devices can comprise a resilient flexible substance inert to bodily fluids.

Devices according to the present invention, can permit cyclic loading in response to cardiogenic blood pressure changes. This is particularly advantageous when used as an intravascular device to repair or support an artery. As a consequence, these devices can withstand fatigue and not fail due to the cycling.

In at least one embodiment, a device can have a strong magnetic polarity (collapsed state) and a weak magnetic polarity (expanded state), for example, to widen arteries that have become narrow over time. The magnetic properties of components of the device are changeable, based on the radio frequency transmitted to them; thus the device can be forced to a larger area or made smaller by means of changing the magnetic properties. The device may also be provide with a unique radio frequency, identification number.

Methods of positioning devices are provided, using a Nuclear Magnetic Resonance (MNR) control system to monitor the positioning of the devices.

Devices methods and systems described herein may be used to repair urinary tracts or other difficult to approach places, which supports the vessel or tract, and can be left in position.

Devices described herein conform well to the tissues that they are attached to and thus, when implanted in a vessel, prevent flow defects, luminal narrowing and occlusion.

Devices, methods and systems described herein can be used to treat and repair abdominal aortic aneurysms without the need for surgical intervention through the abdominal wall.

In at least one embodiment, the device is flexible so it can negotiate bends in the artery, vein and capillaries of a patient as it is being delivered to a target location.

The present methods of implantation are rapid and thus avoid substantial blocking of the flow of blood through the vessels, since the device is rapidly delivered and fixed to the target vessel.

In at least one embodiment, a device is inserted into a patient in a collapsed configuration (e.g., strong polarity condition, smaller dimension) and transported into a vessel in need of repair at a location distal to the damaged vessel wall. The diameter of the patch can be decreased or increased depending on the magnetic polarity controlling the cells within the patch. The invention is useful for electronic controlled transluminal implantation by means of a variably expandable prosthesis for blood vessels, respiratory tracts or such. In surgical and other medicinal procedures there is occasionally a need of interjecting and expanding a device in, for example, blood vessels, urinary tracts or other difficult to reach places that can be left in a location.

The present invention provides a system that produces a cell fabricated patch (synthetic graft), which is transported, controlled and guided by a Nuclear Magnetic Resonance (NMR) positioning systems for placement of the graft in a vessel, which may be a blood vessel or artery.

In at least one embodiment, the device is covered by cell growth within a reasonable time after the fusion of the device to the vessel wall.

Devices described herein may also be used in other structure such as the respiratory, biliary, or urinary tracts to reinforce collapsing structures.

In at least one embodiment, the device is relatively simple in construction, provides easy placement and can be rapidly dissolved in case of emergency.

Methods, devices and systems are provided for less-invasive repair of aortic aneurysms and smaller aneurysms, wherein a prosthetic graft is securely fastened to the wall of the aorta or other vessel without using pins which can cause serious problems that may block the flow of blood through the surgical site during the procedure. This procedure employs a graft, which more securely adheres to the aorta over a larger surface area of healthy portions.

With this invention, the chances of arterial damage and trauma caused by cumbersome, rigid prior art catheters having obscure folded portions, is prevented.

A small patch may be inserted into small blood vessels. Grafts (patches) are insertable through smaller incisions and body openings and may be guided by the master NMR system into and through smaller and more curved canals and passages, and blood vessels in particular. Regarding very small grafts, they are insertable in a small incision in blood vessels of the brain.

The patches (stents) do not have the transverse folds of the prior art devices and are manageable, maneuverable and effortlessly controlled within the blood vessel, canal or passage. They also quickly and non-turbulently change from their collapsed state to their expanded state or various transitionally states. Since the artery is elastic and expands and contracts, the invention conveys the use of material having the same or essentially the same elasticity as the artery. Compliance is another feature of the stent. Compliance is the ability to expand and contract like a natural artery in response to changing blood pressure.

Using the present system, methods and devices, a procedure for performing an aneurysm repair may be performed at medical centers which are not outfitted for superior cardiovascular surgery, thereby reducing the time between diagnosis and corrective surgery.

These and other features of the invention will become apparent to those persons skilled in the art upon reading the details of the system, methods and devices as more fully described below.

DETAILED DESCRIPTION OF THE INVENTION

Figure 1:
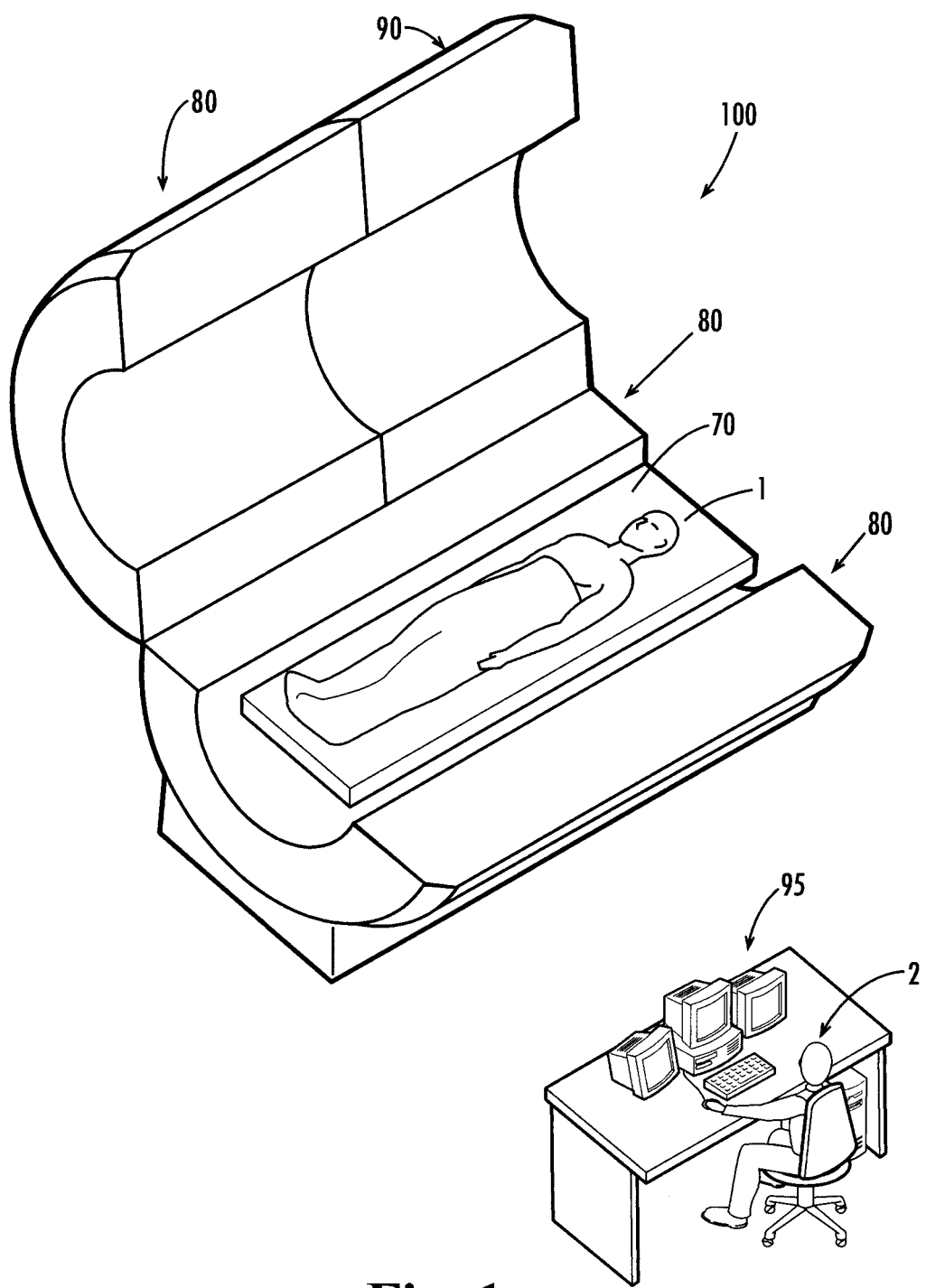
FIG. 1 schematically illustrates an automated vessel repair system according to the present invention.

Before the present methods, systems and devices are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a cell" includes a plurality of such cells and reference to "the device" includes reference to one or more devices and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

The term "aneurysm" refers to a permanent cardiac or arterial dilatation usually caused by weakening of the vessel wall. There are three types of aortic aneurysms, classified by their shape. If the entire circumference of the aorta is involved, it's known as a fusiform aneurysm. If only a portion of the circumference is affected, it's called a saccular aneurysm. If the layers of the aortic wall separate or are torn, allowing blood to flow between the layers, it's called a dissecting aneurysm.

The term "stent" is typically used to refer to a short tube, open at both ends for insertion in a blood vessel following balloon angioplasty to prevent restenosis. Terms other than stent such as graft prosthesis, arterial endoprosthesis, intraluminal graft and intravascular mechanical support may be and are frequently used instead of "stent" to convey the same meaning.

"Micro-Electro-Mechanical Systems" (MEMS), is the integration of mechanical elements, sensors, actuators, and electronics on a common silicon substrate through microfabrication technology. While the electronics are fabricated using integrated circuit (IC) process sequences (e.g., CMOS, Bipolar, or BICMOS processes), the micromechanical components are fabricated using compatible "micromachining" processes that selectively etch away parts of the silicon wafer or add new structural layers to form the mechanical and electromechanical devices.

"Nuclear Magnetic Resonance" (NMR) was described independently by Felix Bloch and Edward Mills Purcell in 1946 both of whom shared the Nobel Prize in physics in 1952 for their discovery. The development of NMR as a technique of analytical chemistry and biochemistry parallels the development of electromagnetic technology. This technique allows the detection of radio frequency energy, and the absorption of such energy by matter.

"Computerized Axial Tomography" (CAT) or "CT" (computed tomography), sometimes called CAT scan, uses special x-ray equipment to obtain image data from different angles around the body and then uses computer processing of the information to show a cross-section of body tissues and organs. Recent technical advances with respect to CT scanners now enable 192 images of the body per second. This non-invasive, virtually pain-free procedure offers exceptional image quality, which can mean better diagnosis, can allow mapping of the anatomy, can facilitate faster recovery time as less invasive procedures may be required, and offers increased patient comfort and convenience.

"Magnetic Resonance Imaging" (MRI) is a unique imaging method because, unlike the usual radiographs (x-rays), radioisotope studies or even Computed Tomography (CT) scanning, it does not rely on ionizing radiation. Instead radio frequency waves are directed at protons, the nuclei of hydrogen atoms, in a strong magnetic field. The protons are first "excited" and then "relaxed," emitting radio signals that can be computer-processed to form an image. In the body, protons are most abundant in the hydrogen atoms of water—the "H" of $H_2O$—so that an MR image shows differences in the water content and distribution in various body tissues.

A "nuclear scan" refers to use of a small "tracer" dose of radioactive material, that is not dangerous to the patient. Once this tracer element is injected into the patient's system, it can be followed through the system as the patient lies directly underneath a sensing device. A nuclear scan is most often used to assess body function. Other uses include measurement of stomach emptying and localization of intestinal bleeding. Nuclear scans require very little preparation.

Devices, Systems and Methods

One of the purposes of the invention is, along with other aspects, to repair weak arteries, vein walls, or other human body vessels. Repairing weak artery walls can prevent aneurysms. An aneurysm is the bulging out of the wall of a weakened blood vessel. If the bulging becomes extreme and stretches the vessel wall beyond its limit, the vessel may rupture. Various types of aneurysms or other degenerate diseases may influence the capability of the human vessels to conduct fluids and in turn may be life threatening.

The present invention employs semiconductor manufacturing methodology, such as, nano manufacturing techniques to produce an internal prosthesis (stent). After producing the stent, the invention allows the detection of the stent (prosthesis), and controlling, positioning and fusing to the vessel wall by means of a Nuclear Magnetic Resonance (NMR) control system. Accordingly, devices such as stents are designed to allow detection, control and positioning thereof within a vessel in need of repair by external guidance, such as the use of an NMR control system, for example.

A graft according to the present invention may be movable from a collapsed (strong polarity) configuration having an expanse less than the diameter of the vessel to an expanded configuration (weak polarity). The expanded configuration is an open configuration in which the graft has a diameter more or less equal to (or slightly greater than) that of the vessel wall in need of repair. The collapsed configuration reduces the radial dimension of the graft (relative to the expanded configuration), without producing oblique or transverse folds and/or wrinkles in the graft.

A device according to at least one embodiment of the present invention can also be used in medical applications other than arterial aneurysm repair. As mentioned, it may be employed in miscellaneous types of aneurysm prevention reflected by some form of vessel widening, or the opposite, stenosis, which involves contraction of blood vessels. The invention can be used to sustain and keep open vessels of venous systems, to close pathological vessel deficiency. The invention can also be used to bridge pathological vessel dilatations and ruptures in interior vessel walls or to brace bronchial tubes and bronchi.

A device according to the present invention is made of material tolerated by the human body, and can be applied within, or replace part of, for example, blood vessels in the body of a living animal, a living human or some other intricate accessible place within either. The graft material may be resiliently flexible and is substantially inert to bodily fluids.

Grafts according to the present invention also permit cyclic loading in response to cardiogenic blood pressure changes, without degradation of the graft. As a consequence, the graft will not fatigue and fail.

In at least one embodiment, stents (patches) can have a relatively strong magnetic polarity in the collapsed configuration and a relatively weak magnetic polarity in the expanded configuration. In the expanded configuration, such stents can be used to widen arteries that have become narrow over time, for example. The magnetic properties of the patches are changeable, based on the radio frequency transmitted to them; thus the patch can be forced to a larger area or made smaller by means of changing the magnetic properties of each biocompatible semiconductor cell and patch (stem). Each stent (patch) and cell will also have a unique radio frequency identification number.

A Nuclear Magnetic Resonance (MNR) control system can be used to monitor the positioning of the stent and the tubular graft and to control delivery thereof.

The present invention does not require the use of anchoring rods, anchoring pins, a plurality of staples, flexible tubular bodies, extending rods, NITINOL® wires, wire loops, helical springs and coils on the graft or other vessel piercing facilities. Thus, the present invention eliminates risks that may be imposed by piercing the wall of the vessel with these devices. These anchoring pins, wires, tubular bodies, coils, staples and extending rods can be extremely dangerous and stretch the vessel wall beyond its boundary. These pins, wires, coils, may penetrate the vessel wall, causing the vessel to rupture and result in serious injury or death to the patient.

Turning now to FIG. 1, an automated vessel repair system 100 is schematically shown. A patient is positioned on a table 70, with elements of the NMR machine 80 below and above him/her. The patient 1 is almost fully enclosed by the CAT scanning 90 and NMR 80 machines technology. The top of the system 100 is a clamshell arrangement, with the forward portion 90 containing CT/MRI equipment configured to perform CT/MRI scans. The rearward portion 80 contains NMR equipment, which, in combination with NMR equipment 80 in the lower portion of system 100 is configured to perform nuclear magnetic resonance functions. Both CT/MRI and NMR machinery are currently available as known to those of ordinary skill in the art. The upper clamshell is configured to move back and forth (forwardly and rearwardly) over the patient 1 in directions toward the head (forward) and the feet (rearward) of the patient, so that either portion 80 or 90 can be located over any desired location of the patient 1. These elements of the repair system 100 allow control of the patches 10 during delivery thereof and provide the RF energy and communication information transmitted to the patches 10.

Also illustrated are the control panel 95 and operator 2 of the repair system 100. In this example, the operator 2 is sitting at the system console 95 monitoring the patch/device 10 being guided to an intended target location within the body of the patient 1. The system 100 includes sub-sections: patch assembly, patch delivery, patch positioning, and patch fuse technology, located throughout the main chassis of system 100, below and above the patient 1.

System 100 may be used to insert the graft device 10 in its collapsed configuration (strong polarity condition, smaller dimension) into the vessel in need of repair. The diameter of the patch e.g., graft stent or prosthesis) device 10 can be decreased or increased depending on the magnetic polarity controlling the cells 20 within the patch. The invention is useful for electronically controlled transluminal implantation by means of a variably expandable prosthesis 10 for blood vessels, respiratory tracts or such. In surgical and other medicinal procedures there is occasionally a need of interjecting and expanding a device in, for example, blood vessels, urinary tracts or other difficult to reach places that can be left in a location.

Device 10 can thus be implanted by system 100, as the cells 20 thereof are transported, controlled and guided by Nuclear Magnetic Resonance (NMR) positioning system 80 for placement of the cells 20 of graft 10 in a vessel, which may be a blood vessel, artery or other vessel in the body. This external guidance ensures the device 10 is placed in an intended location, by minimally invasive procedures, and the device 10 can then be covered by cell growth within a reasonable time after the fusion of the device 10 to the vessel wall. As already noted, these devices 10 and procedures are not limited to use in blood vessels, but may also be implanted in other vessels or ducts, including, but not limited to: respiratory, biliary, and urinary tracts to reinforce collapsing structures or to open a closed or partially closed passageway.

Device 10 is relatively simple in its construction, and provides easy placement and can be rapidly removed by guidance and withdrawal using the NMR system 80 in the same manner that it is used to guide device 10 into place for implantation. Thus, device 10 can be withdrawn from the surgical target location and the patient by guiding it out of the patient in an integrated configuration, using the NMR system 80.

Figure 2:
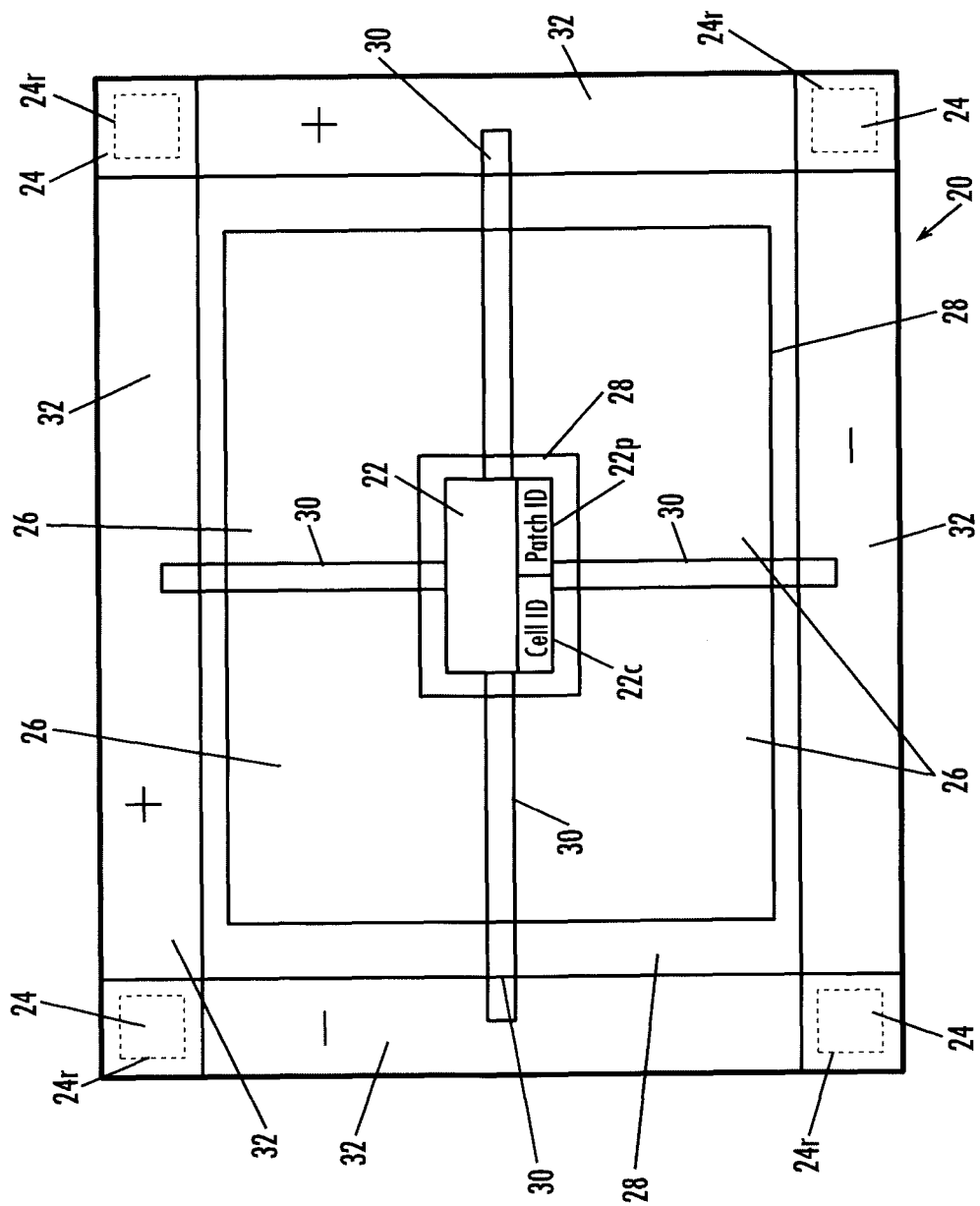
FIG. 2 is a schematic illustration of a biocompatible semiconductor cell.

Referring now to FIG. 2, the basic structure of a biocompatible semiconductor cell 20 is illustrated. The size of the cell varies dependent upon the size of the stent 10 required. In one example, a cell 20 has dimensions of about 50 microns length by about 50 microns width by about 20 microns thickness, up to dimensions of about 0.2" length by about 0.2" width by about 500 microns thickness, although dimensions can vary. The center area 22 contains the communication element of the cell 20. Radio frequency energy is transferred from the master NMR apparatus 80 to the cell 20 through this element 22 of the cell. The cell and patch RFID information is transferred through this communication element 22. The communication element 22 has the capability of being programmed for a unique number. For example, each of multiple cells 20 used to make up a device 10 can be provided with a unique radio frequency identification code or number (RFID). Additionally, the overall device 10 may also be assigned a unique RFID.

The radio frequency polarity information from the master NMR machine 80 is also transferred through communication element 22. A change in the radio frequency controlling the polarity will change the distance between each cell 20 and change the overall dimensions of the device 10 (also referred to as patch or stent).

Each corner of the cell 20 has an NMR position element 24, as well as a radioactive trace substance 24r. Positioning elements 24 are controlled by master NMR machine 80 to move and guide the cells 20 within the subsections of the system 100 and later, through the body. After the cells 20 are assembled into a patch (stent) device 10, the outer most corner cells 20 are assigned designated patch corner or patch positioning elements 24. For example, if device 10 is to be formed as a sheet, the four corners of the sheet will be assigned the designated positioning elements. If device 10 is tubular, two cells 20 at a proximal end of device (e.g., diametrically opposite elements) can be assigned with designated positioning elements, and two cells 20 at a distal end of the device can be assigned with positioning elements 24. It is noted here that other variations of assignment schema can be used, as each cell 20 can be provided with positioning element capability, as noted above. Positioning elements allow the NMR system 80 to guide and control the patch 10 through the body. When a patch device is being assembled, elements 24 are used to arrange the cells in a desired order that they are intended to be arranged in for integration to form the patch device 10. After the patch device 10 is assembled, the elements 24 of the outer most cells (i.e., perimeter cells—corner cells for a flat patch device, end cells for a tubular device) are controlled by the NMR machine 80 for coordinated movement and delivery of the entire device 10.

Fusion portions 26 are provided on cell 20. Fusion portions 26 are configured to receive radio frequency energy after the patch (stent) 10 is positioned within the vessel under repair to fuse the patch to the vessel wall. Fusion portions 26 can be made from biocompatible semiconductor materials molded from porous silicon, for example. Alternative materials for fusion portions 26 include, but are not limited to: carbon nano structure and devices such as carbon nanotubes. In use, the fusion portion heats up and fuses to the tissue (e.g. vessel wall, or other tissue at the surgical target location). NMR machine 80 transmits RF energy in a coordinated way according to mapping information provided by the CT scan, to which the NMR machine is registered. In this way the transmitting portion of the NMR machine 80 can drive device 10 along an intended pathway inside the patient 1. The transmitting portion of NMR machine 80 also provides RF energy to particular cells 20 to polarize the cells 20 so that they magnetically attract to one another to integrate the cells 20 into an integrated device 10.

Isolator portions 28 surround the communication element 22 and the fusion portion 26, to protect communication element 22 and the portions of the cell outlying the perimeter of the fusion portions 26 during the fusing process. Isolator portions 28 may be made from biocompatible, insulating materials that do not conduct heat efficiently, and preferably also do not conduct RF energy. For example, isolator portions 28 may be made from biocompatible polymers, polymer foams, bioceramics, or other insulating, biocompatible materials.

Communication links 30 electrically connect communication element 22 with polarity regions 32 to send polarity intensity frequency energy received by communication element 22 to the peripherally located polarity regions 32. As shown in FIG. 2, each cell 20 may include four polarity regions 32, one on each side. Alternatively, cells 20 may be formed to have three, or more than four sides, in which case polarity regions can be provided along each side of the cell, at the periphery. Communication links 30 each include an on/off polarity switch from the link section to the polarity section. Each on/off polarity switch comprises a semiconductor switch having on and off states, which can be switched between by remote control, using RF energy transmitted by NMR machine 80. Each of these switches has a unique identifier, so that NMR machine 80 can individually/independently control the switches.

Figure 3:
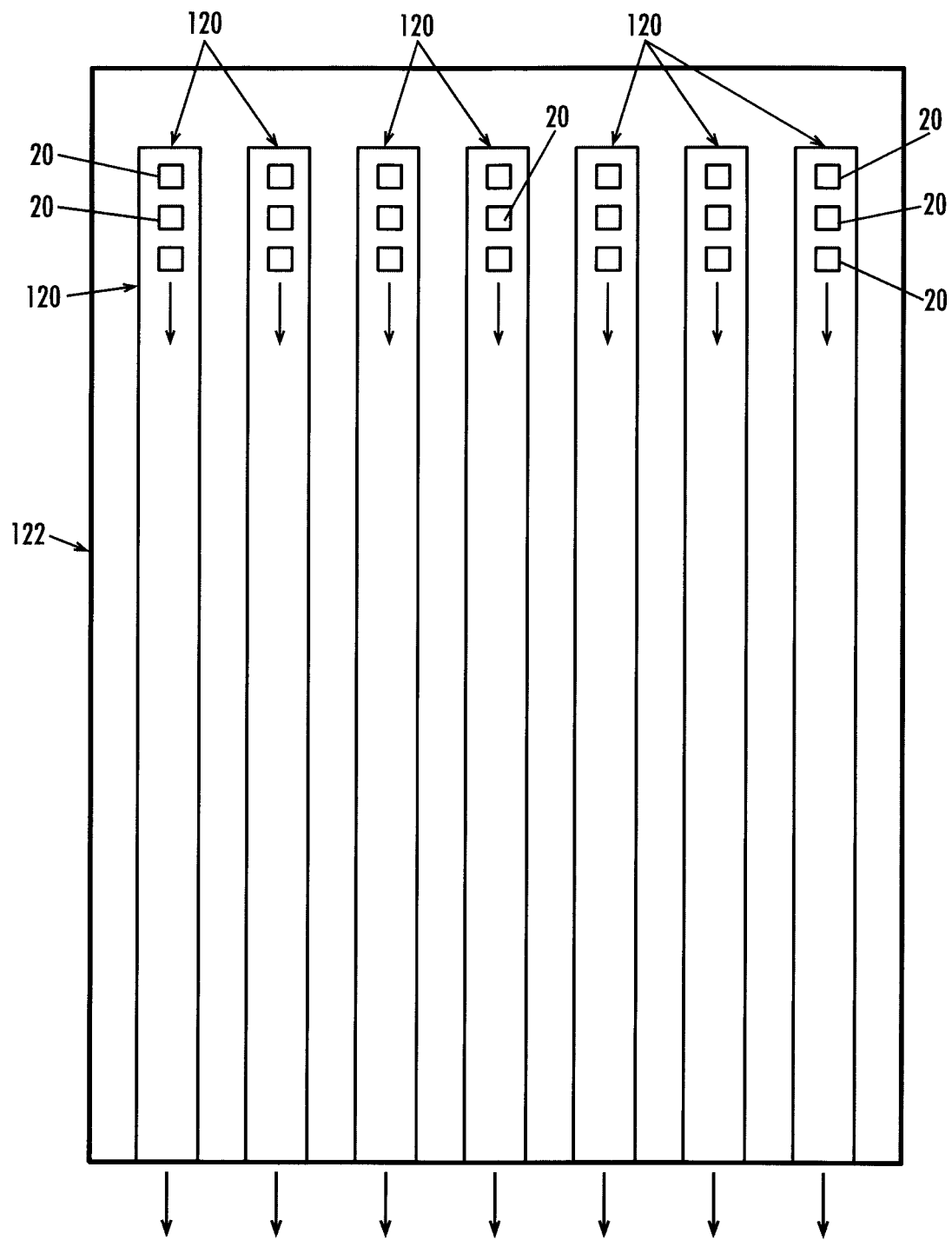
FIG. 3 illustrates semi-conductor cells placed in ministrips.

Referring now to FIG. 3, semi-conductor cells 20 are shown placed in mini-strips 120, which may be elongated tubular containers, or elongated open channels, for example. The manufacturer of the bio semiconductor cells 20 arranges the cells 20 in the containers/mini-strips 120 after they are manufactured, tested and marked, etc. The strips 120 of cells 20 are also placed in a tray 122 as indicated, which allows easier placement into the assembly receiving area in the sub-assembly unit of the system 100. The outputs of the mini-strips 120 feed the input to the assembly receiving area (such as by gravity feed, for example), in the direction of the arrows shown at the bottom of FIG. 3.

Figure 4:
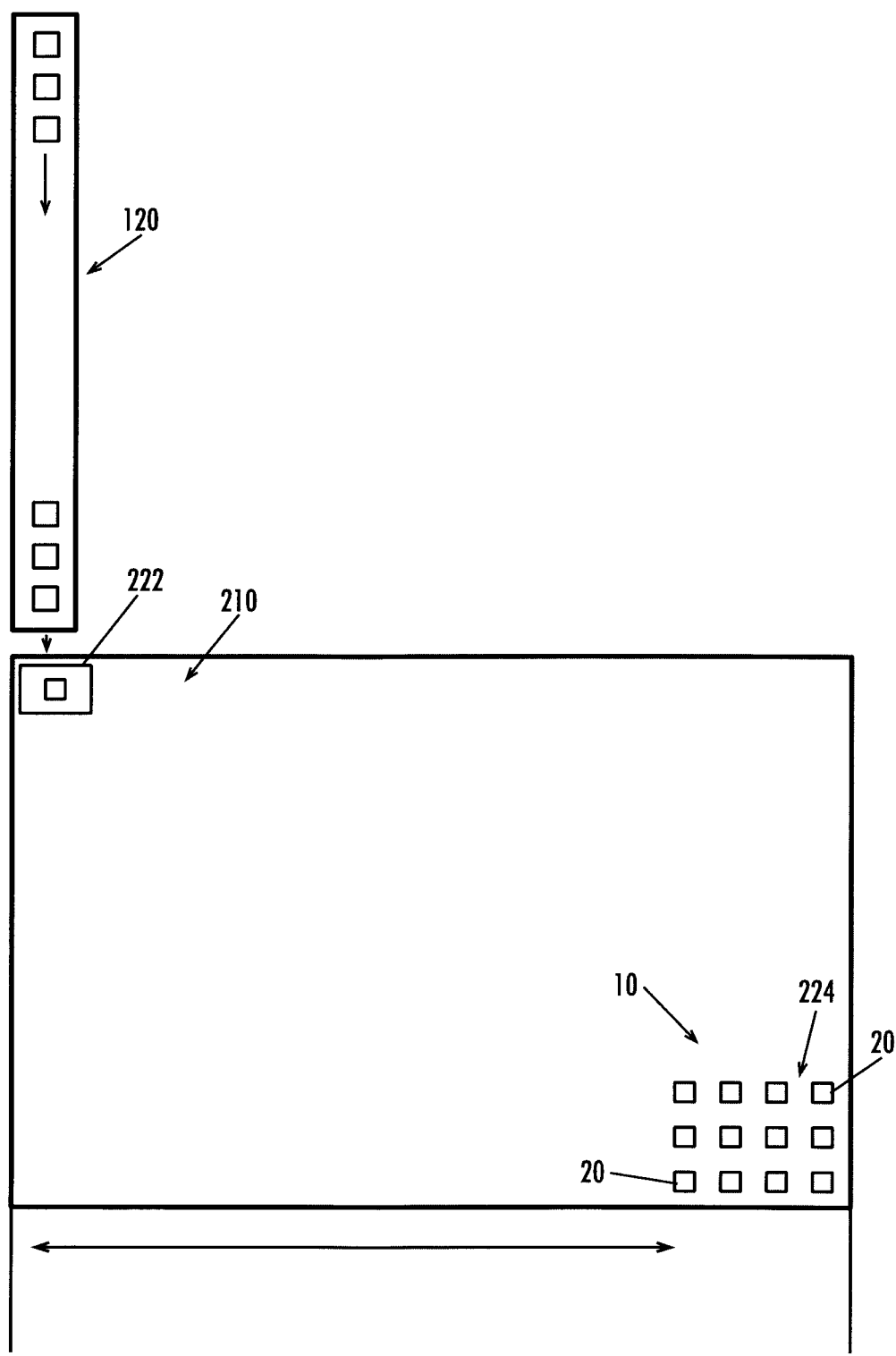
FIG. 4 schematically illustrates a mini-strip containing cells with the output end of the mini-strip being placed into alignment with the input location of a patch assembly subsection.

FIG. 4 schematically illustrates a mini-strip 120 containing cells 20 with the output end of the mini-strip 120 being placed into alignment with the input location of the patch assembly sub-section 210 of system 100. Only one mini-strip 120 is shown in FIG. 4, for simplicity of illustration. In practice, multiple mini-strips 120 can be, and typically are inputted in parallel to the input location of the patch assembly sub-section 210. As noted, the manufacturer of the bio semiconductor cells 20 arranges the cells 20 in the mini-strip containers 120. Thus, the owner/operator of the master machine 100 can purchase the cells 20 conveniently packaged in this manner.

Each biocompatible cell 20 must first be tested, ensuring proper operation of the cell 20. Accordingly, when a cell 20 has been positioned into the input programming section 222 of the patch assembly area 210, the first step is to test the cell 20 for suitable performance. If the cell 20 fails the testing process, it is removed from the input programming section 222 and discarded or recycled. Cells 20 that pass the testing phase are now ready to be programmed with a unique RFID. As indicated earlier, the communication and RFID element 22 located in the center section of the cell 20 receives the information with respect to the unique code and establishes this information internal to the cell 20.

Within the patch assembly area the cells 20 are arranged internal to this region using the cell RFID and corner positioning information programmed into each cell 20. One-by-one the cells 20 are moved and placed into the newly formed patch 10, illustrated in the bottom right corner of the patch assembly area 210 shown in FIG. 4. With improvements in controlling software, cells will be capable of being moved one row at a time during assembly into the patch assembly area. Cells 20 are each provided with a unique identifier (ID, such as numeric, alphanumeric, etc.) as noted above, so that NMR machine 80 can move each cell independently by apply a directed RF field thereto with the unique ID for that particular cell. By using the unique ID, the magnetic force applied by the NMR focuses only on the cell having that particular unique ID. The other cells 20 are not magnetic, until they are turned on by application of the particular unique ID assigned thereto. Thus, semiconductor switches can be turned off or on to make a particular cell respond to a magnetic field or not respond thereto, according to whether or not particular semi-conductor switches are turned on or off. Thus, the combination of the unique ID and control of particular semiconductor switches determines whether an electromagnetic property of a particular cell is turned on or off.

FIG. 4 shows an example of a patch or device 10 constructed of twelve cells, in a four column by three row arrangement. Of course, other sizes and shapes of devices 10 could be constructed, as needed, including, but not limited to, tubular devices 10. After the patch is assembled 10, the master NMR 80 assigns the patch 10 a unique RFID number. Every cell 20 of the patch 10 now contains this unique RFID patch number, with each cell also retaining its individual RFID number. This unique number (Patch RFID) and the radioactive tracer elements 24r can be used to guide the patch 10 from now on and later within the person in need of surgery. The position elements 24 are used to assemble the device 10 as noted, as each cell 20 has elements 20 designated with respective positioning designations (e.g., top/right, top/left, etc).

The exemplary patch 10 indicated in FIG. 4 is very small, on the order of about 200 microns by about 150 microns. The patch assembly area 210 is capable of assembling much larger patch, perhaps as large as about 4000 microns by about 4000 microns. NMR machines that require larger patches can be outfitted for this capability. The newly assembled patch 10 is next ready to be transferred from the patch assembly area 210 to be implanted into the body of the person requiring surgery.

Figure 5:
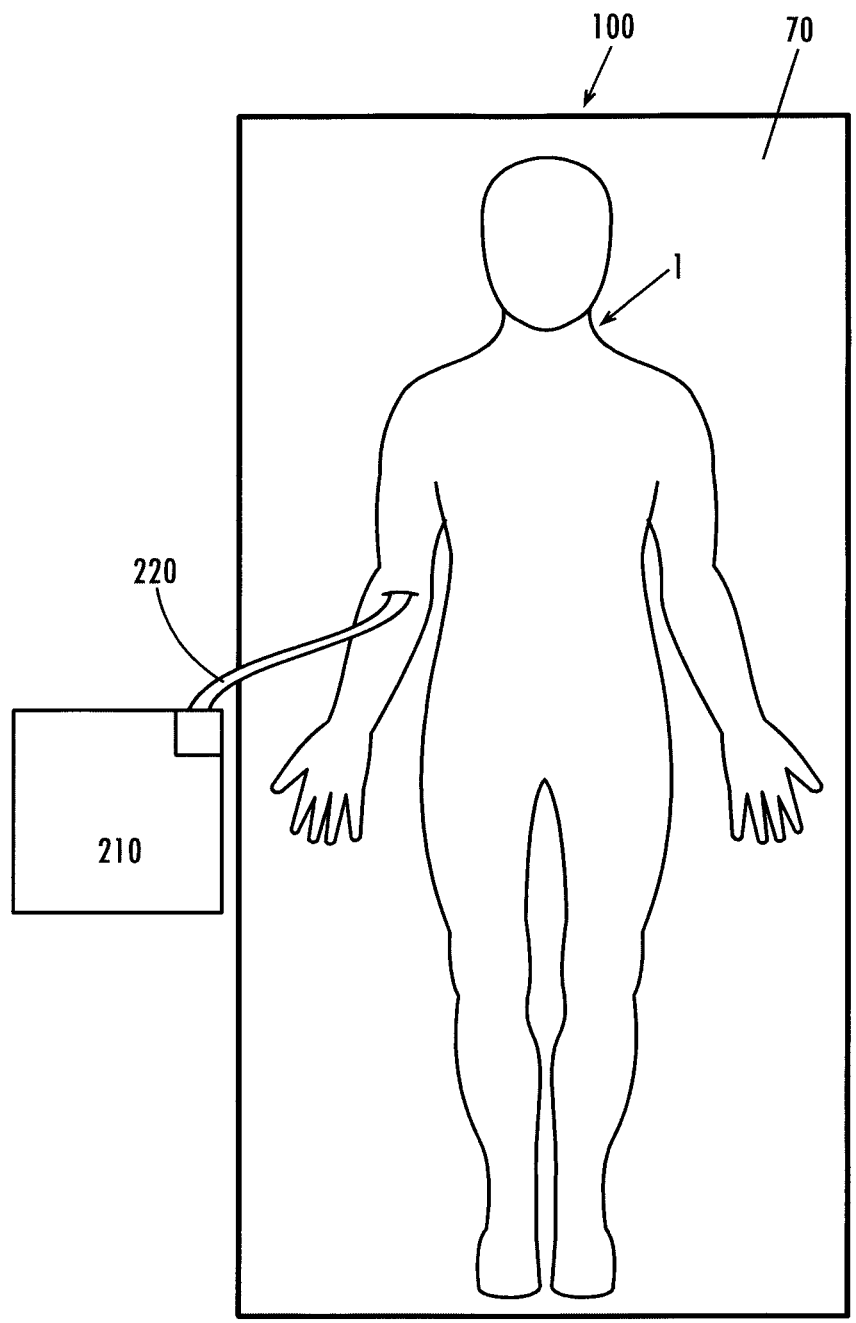
FIG. 5 illustrates a patient lying on a table of the system.

FIG. 5 illustrates a patient 1 lying on table 70 of system 100 with an (intra-venous) IV device 220 having a lumen with an inside diameter large enough to allow device 10 in the collapsed configuration to be passed therethrough and into the patient 1, via an artery, vein, or other vessel. The patch (stent) 10 from the output of the patch assembly sub-section 210 is guided down the tube of IV device 220 by the master NMR machine 80. The unique RFID of the patch 10, plus the radioactive tracer element 24r, allows the master NMR device 80 to comprehend the precise position of the patch 10 as the patch 10 is guided down the connection tube and into the artery or place of insertion.

Figure 6A:
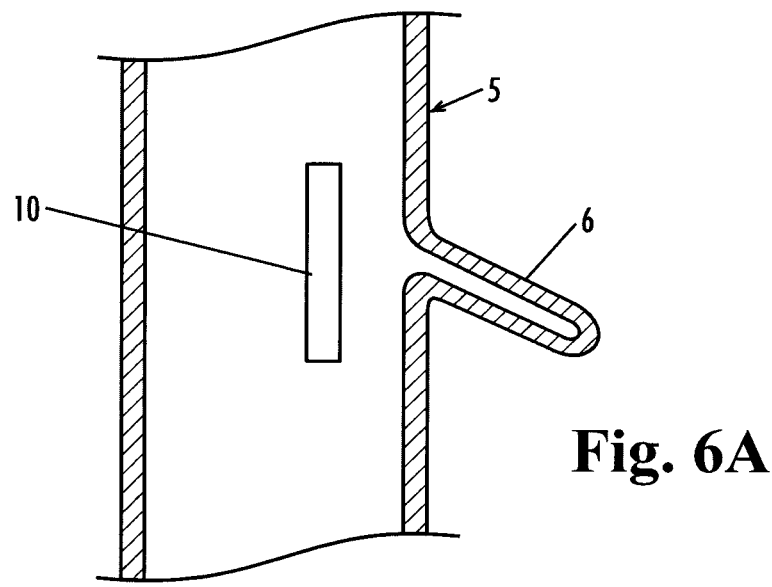
FIG. 6A illustrates a device being guided and positioned by NMR guidance from the system to a target location over an aneurysm in a vessel.

FIG. 6A illustrates device 10 being guided and positioned by NMR guidance from system 100 to a target location over an aneurysm 6 in vessel 5. The master NMR machine of system 100 is used to precisely transport device 10 through the body of the patient to a target location where the device 10 is to be implanted. By registering movements of devices 10 to a three-dimensional map of the body constructed previously by use of the CT machine 90, NMR machine 80 is able to precisely locate and track devices 10 (multiple devices 10 may be tracked, located and moved at the same time based upon the unique RFID of each device 10 and, optionally with the use of radiation tracers. The coordinates of each repair location are programmed into the master machine computer of system 100 and are uniquely identified. The system 100 allows for slight movement of the patient, and adjusted positioning of the patch 10 as needed, as the patient 1 cannot be expected to remain perfectly still in outpatient style procedures where general anesthesia is not applied. In operating room settings, general anesthesia can be applied to the patient.

Figure 6B:
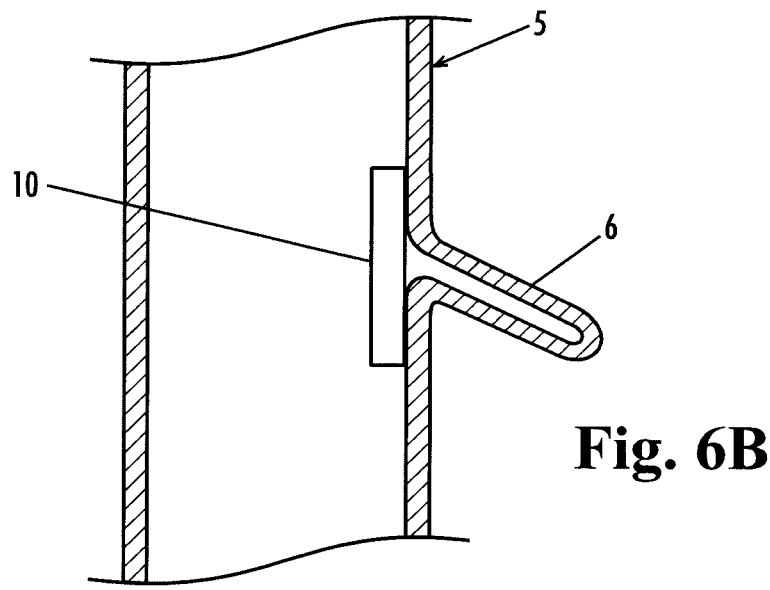
FIG. 6B illustrates the device of FIG. 6A having been contacted to the wall of the vessel.

Once device 10 has been positioned over the target location as intended, system 100 guides device into contact with the wall of the vessel 5, as illustrated in FIG. 6B. System 100 then transmits RF energy to the fusion section 26, vial control element 22 of each cell that makes up device 10. This causes the fusion sections 26 to heat up and fuse to the wall of vessel 5, thereby sealing off the aneurysm 6.

Construction of Bio-Semiconductor Cells

The manufacturing of the individual biocompatible semi-conductor cells 20 is facilitated by nanotechnology techniques performed by semiconductor manufacturing facilities.

Cells 20 are assembled, to emerge as a stent prosthesis 10. Nanotechnology or semiconductor technology manufacturers apply microelectromechanical systems (MEMS) building blocks, which form the stent (patch) 10. Microelectromechanical systems (MEMS) devices integrate physical, chemical, and even biological processes in micro- and millimeter-scale technology packages. MEMS devices are now used in many sectors: information technology (IT), medicine and health, aerospace, automotive, environment and energy, to name a few. On the horizon is the development of nanomanufacturing technologies that will support tailor-made products having functionally critical nanometer-scale dimensions using massively parallel systems or self-assembly.

Cells 20 can be manufactured independently by semiconductor manufacturers and then purchased by the administrator/owner of a system 100. The optimum quality and the materials employed for the biocompatible semiconductor cells can be jointly determined by the semiconductor manufacturer's material scientists, proprietors of the system 100 and other technical specialists. Ongoing dialog will determine the foremost semiconductor cells 20 available.

Stents 10 having dimensions as small as about 100×100×50 microns can be assembled. Smaller (stents) patches 10 made of smaller cells may be necessary for smaller vessel repairs. The size of the cells 20 and stent (graft) 10 is determined by the size of the area of the vessel in need of repair, as well as, potentially, the inside diameter of the vessel to be repaired.

Cells 20 can be shipped in mini-strips 120 designed to be placed to feed patch assembly unit 210 within the NMR control apparatus of system 100. Cells 20 of varying dimensions can be shipped in different proportion strips (e.g., strips of varying lengths and/or cross-sectional size or shape). Additionally, or alternatively, strips 120 carrying different sized cells 20 may be colored coded differently from one another. The NMR control apparatus 80 can be configured flexibly enough to receive many sizes of strips 120 with different proportions of biocompatible semiconductor cells 20.

Decision-makers will determine the best prosthetic arterial substitutes in humans to rectify diminished arterial flow. Decision-makers will determine if stents of polyester, polytetrafluoroethylene and/or other synthetic materials are to be used when the diameter of the arterial surrogate is ordinarily greater or equal to six millimeters. Normally, synthetic vascular prostheses with diameters less than six millimeters have not been customarily used, generally because of the increased likelihood of the outgrowth of hindrance due to thrombosis and/or vessel wall thickening.

Decision-makers, material scientists, medical professionals, etc., may collaborate to determine the best cardiovascular implants 10, including materials and sizes to be used for particular vessel defects to be repaired. The contact surface of the stent (patch) 10 must have high blood adaptability (anti-thrombogenity). Device 10 may optionally include a coating of a material, such as silicon carbide, principally with an amorphous layer fabrication, to facilitate blood compatibility. Further, device 10 must have good plastic ductility to allow it to be distorted during implantation and fixation to a vessel.

The base material or bio semiconductor substrate of cell 20 may include high-grade steel, such as surgical grade stainless steel, a titanium alloy, a tantalum alloy, nickel-titanium alloy and/or platinum/iridium alloy, for example. The deposition of good inorganic coatings in normal discharges requires substrate temperatures in excess of 250 degree C. (too elevated for most plastic substrates).

One technique for reducing deposition temperatures required is through the use of high intensity pulsed radio frequency plasma techniques. A process is illustrated in published UK patent application No. 2105729A (R. A. H. Heinecke-S. M. Ojha-M. J. Cooke 30-2-2), which is hereby incorporated herein, in its entirety by reference thereto, and describes a process for surface processing a heat sensitive substrate material; encompassing exposing the surface of the substrate to a high power radio frequency pulsed plasma of low average power. The plasma pulse provides a power density of at least a few kW per liter. In general, the pulse strength is adequate to accomplish full dissociation in the reactant gas. Other substrate materials are successfully fabricated from silicone rubber, polyacrylics, polypropylene, polyesters, polyfluorocarbons, and polyvinyl chloride.

Bio-semiconductor cell 20 may be fabricated utilizing the latest state of the art manufacturing techniques, and the employment of multi-component mixtures of process gases, and pulsation temperature/time methodology. Additional techniques of using pre-decided flow rate and combination of power with a prearranged, second power concentration of materials will be used.

Manufacture of cells 20 may also use improvements regarding to changing vapor pressure, and frequency of the plasma discharge to optimize the manufacture of the cell 20 and improve the biocompatibility of cell 20. The fabrication of the bio semiconductor cells 20 may use methods that are especially advantageous with respect to vascular graft substances in order to create grafts that are both thrombi- and emboli-resistant. Preferably both the substrate material near the contact surface (i.e., surface of cell 20 that will contact the vessel wall when device 10 is implanted) and the boundary surface are essentially free from oxygen and hydrocarbons, which is partially subject for the good adhering of the cover layer (e.g., growth of intima over device 10). The bio-semiconductor substrate must be essentially inertia-free due to the heating phase (fusion phase) when the patch (stent) 10 is fused to the vessel wall.

The size of the stent 10 required is determined, at least in part, by the magnitude of the vessel wall in need of repair, as well as the size of the defect to be repaired. For instance, for a capillary in the brain, a patch of only 1000 microns by 1000 microns (250 microns deep) may be necessary. For an aortic stent the patch size may be 50,000 microns by 50,000 microns by 10,000 microns. Accordingly, various sizes of biocompatible semiconductor cells 20 may be manufactured for use in constructing varying sizes of devices 10.

Each cell 20 can be polarized so that the polarity region 32 at the top and right side portions 32 of the cell 20 (see FIG. 2) have a relative positive charge, while the bottom and left side portions 32 have a relative negative charge. Each cell 20 is also provided with a communication/RFID element (center area) isolated from the top/bottom, left/right charge and fusion areas, as noted above. Communication element 22 contains semiconductor switches, which, in conjunction with the cell and patch RFIDs, determine if the proper cell 20 and patch 10 respond to the RF polarity energy sent by the master NMR machine 80. The semiconductor switch may be provided as a static RAM, six-transistor cell, as to ensure no unintentional changes of the semiconductor switch. If the cell 20 and patch 10 RFID switches are turned off, the RF polarity energy has no effect with respect to the polarity charge on each portion the cell 20 or patch 10.

As also noted above, each cell 20 is provided with a communication link 30 from the central communication element 22 to each of the four polarization areas 32. The link 30 to the polarization area includes a semiconductor on/off switch. Depending on whether it is on or off, this switch permits or prevents alteration of the polarization section that it connects with, with respect to the degree of polarization. It is possible to change the top and bottom polarity, but not the left right polarity; the four polarization link switches control this feature.

Each cell 20 includes an RFID code area within communication element 22 that includes a unique RFID code 22c for the cell, and an RFID code 22p for the device/patch (which each cell 20 in the device 10 has) and other communication control information. The bio-compatible semiconductor cell 20 also may be provided with a small "tracer" dose of radioactive material 24r, at a radiation level that is not dangerous to the person undergoing surgery. This radioactive material on the semiconductor cell will enhance the master NMR machine's capability in tracking every patch 10 within the body. The combination of the RFID of each patch 10 and the radioactive material on the patch 10 allows comprehensive discernment of the patch 10 inside the body and the vessel under reformation.

Cells 20 can be polarized using RF energy. A frequency range of energy can be used to determine the degree of polarization of the cell 20. This allows changing the dimensions of the patch 10 at any time. The polarity sections 32 of the semiconductor cell 20 can be doped accordingly, providing enhanced regions and depleted regions to permit alteration of the intensity of polarity. Each of the cells 20 can have a strong magnetic polarity (collapsed state) and a weak magnetic polarity (expanded state), or somewhere in-between depending upon on the requirement of the vessel repair procedure. Alternatively, patches 10 can be formed with set dimensions during assembly using cells 20 which do not change polarities or intensities of polarities.

For cells 20 that have polarization sections (portions) 32 that can vary in relative strength of polarity, each polarization section 32 of each biocompatible cell 20 is provided with a semiconductor switch, which provides the feature of locking in the degree of polarity to that polarization section 32. Increasing the degree of polarity will require the appropriate polarity switch to be turned on. RF energy is then transmitted to the appropriate section through the communication section 22 and link channel 30. The change in RF energy frequency to the communication element 22 of the cell 20, through the link 30 to the polarity element/portion 32 will increase or decrease the polarity of the section receiving the energy. Once the degree of polarity is set, the switch controlling the polarity receiver is turned off. Later, the polarity switch may be turned on again to increase or decrease the degree of polarity for each section. Also, each polarity section of every cell may have different degrees of polarity.

The master NMR machine 80 assimilates the position of each polarity switch in every section 32 of every cell 20 of every patch 10 under the control of the system 100. The programming software of system 100 is designed to permit one or more CPUs of system 100 to keep track of all information monitored with regard to of each cell 20 and each patch 10, and directing a multitude of cells 20, a multitude of patches 10 with different degrees of polarity at the same time. Patches 10 are each assigned a unique number (RFID), as noted above, and top-bottom-left-right coordinates, via positioning elements 24 of designated cells 20, which will allow the NMR system 80 to guide, control and position the patch 10 within the vessel.

Transfer of Bio-Semiconductor Cells

The cells 20 may be gravity fed to supply them to the programming section 222 of the patch assembly section 210 of the system 100. At section 222, the cells are programmed with unique RFIDs, as multiple cells 20 to be used in the same device 10, are each programmed with its own unique cell RFID 22c, and also programmed with the same patch RFID 22p, as noted above. After this programming, the cells are controlled by magnetic forces and are moved by an applied magnetic field that is specific to only the cell whose cell RFID is included with the controlling field. In a typical configuration, the input programming section 222 is located at the output of the mini strip trays 120 containing the biocompatible semi-conductor cells 20.

Until the semi-conductor manufacturers demonstrate a quality level of plus or minus six sigma (three failures per billion units), each semi-conductor cell 20 must be thoroughly tested before it is sent to the patch assembly area 210. The cells 20 must be tested for the ability to communicate with the NMR master machine 80 before they are sent to the patch assembly area 210. The cells 20 must be able to program a unique RFID; both cell 20 and patch 10 ID. For cells that are to be used to construct devices 10 that are transformable between a collapsed configuration and an expanded configuration, each of the cells 20 must be able receive variable frequency signals which control the polarity intensity of each left, right, top, bottom polarization portions 32 of the cells.

At all times, the control section of the system 100 monitors the movement of the cells 20 on the conveyor 252. As noted, each bio-compatible semiconductor cell 20 may contain a small "tracer" dose of radioactive material, in an amount that is not hazardous to the individual undergoing surgery. This characteristic, associated with the RFID capability, allows the master NMR to assimilate the precise location of the patch at all times. The use of radiopaque material is optional, as tracking can be formed solely via RFID's. The radiopaque material allow for a dual tracking capability.

A subordinate component 254 at a feeding location will transfer the cells 20 from the conveyor system 252 to the patch assembly section 210 where the patches (stents) 10 are assembled at location 224.

Assembling Device from Cells

The layout of the individual cells 20 which form stents (patches) 10 according to this invention will be readily understood by those skilled in the art of semiconductor manufacturing and a detailed description is not needed. System 100 controls NMR master machine 80 to integrate cells 20 into a stent (patch) 10 by use of a plurality of biocompatible semiconductor cells 20 by virtue of the opposite polarity of the cells according to the physical laws of attraction and repulsion. As indicated above, each cell 20 is provided with polarity sections 32 (e.g., four for the four-sided cell shown in FIG. 2) permitting attraction between adjacent cells 20. This feature allows the individual cells 20 to be combined into many different varieties depending upon the prerequisites of the operation. This also allows a method of arranging a plurality of cells 20 to form a bio-semiconductor stent 10, by joining and matching the cells 20 according to a program mapped into the main computer of system 100 after the analysis phase of the overall artery repair procedure.

Integrated circuits are typically formed from many small fabrication sections, which are typically termed blocks. Efficient manufacture of the integrated circuits requires that the individual blocks be designed so that, other factors being equal, surface areas are minimized. The bio semiconductor stent 10 is formed from many cells 20 and the cells 20, which need not have the same size, have to be arranged suitably with respect to each other. Several techniques may be employed to assemble the individual stents (patches) 10. The cells 20 of each stent 10 can be electrically connected to each other using different frequencies, which will control the physical attraction and repulsion of the individual cells 20 to each other. However, for the stent 10 to be "stretchable" (i.e., to give the cells 20 the ability to increase distances therebetween, while still remaining attracted to one another to maintain the integrity of the device 10), constraints between every pair of cells 20 must be derived. The derived constraint set is called the closure constraints. A constraint refers to an inequality relation between two cells 20. Accordingly, methods for reducing the number of constraints may be used, i.e., the size of the closure constraint graph or set polarity, is critical. Expectations are that these conditions of polarity must constitute uniformity to reduce constraints between the cells.

Devices (patches) 10 can be assembled according to the information programmed into system 100 to control the master NMR machine 80. The sizes of the patches (stents) 10 are determined by the size of the area in need of repair. The controlling computer of the master NMR machine 80 can be programmed with respect to the algorithms required to maintain systematization of the sequence of each vessel repair process.

After a device 10 is assembled using individual cells 20, the device 10 is programmed with respect to the corner positioning cells, upper right, upper left, lower right, lower left, etc. (or opposing cells 20 at proximal and distal end in the case of a tubular device), at noted above, to be arrangement cells. This is done through the communication element 22 of the bio cells 20 in conjunction with the unique RFID of the appropriate cells 20. This positioning information is used later to navigate and position the device 10 over the area of the vessel in need of repair.

Also, each corner of the cell 20 has an NMR position element 24, as well as, optionally, a radioactive trace substance 24r, this corner section is used by the master NMR 80 to track the assembled device 10 and guide it through out the process.

In some cases, a patient may require a plurality of devices to be implanted. It would not be unexpected for a patient 1 to require ten or twenty stents during the repair procedure, for example. In such a case, the NMR machine 80 of system 100 can coordinate operations, using algorithms programmed within the controlling computer of system 100 to move, place and fuse each stent 10 during the operation. With each patch 10 having a unique RFID and trace radioactive element, the controlling computer will be able to track and position multiple patches 10 at the same time. By use of the polarity sections (four) of each cell 20, the patch dimensions can be changed at any time. Utilizing the link and polarity switches permit this characteristic.

Delivering a Device

An analysis of one or more surgical target areas is first performed, prior to assembly or delivery of one or more devices 10. The CT machine 90 including technical features in concert with pixilated scintillation detectors, as known in the art, is used to scan at least a portion of the patient 1 that includes the surgical target area(s) as well as including a portion of the patient that includes one or more pathways from an external location on the patient to the surgical target area(s). This scanning process provides a three-dimensional map of the vascular system, respiratory ducts, or any other structures along which a device or devices are to be delivered, as well as the surgical target location(s). Accordingly, this map or maps are analyzed to determine the best delivery routes for delivery of one or more devices. An example of use of this scintillation detection technology for analysis of the circulatory system is described by A Kastalsky et al. in "Semiconductor high-energy radiation scintillation detector", Nuclear Instruments and Methods in Physic Research A, Elsevier B. V., 565 (2006) 650-656, which is hereby incorporated herein, in its entirety, by reference thereto.

The scintillators detect high-energy radiation through generation of light, which is subsequently registered by a photo-detector, typically a photo-multiplier that converts light into an electrical signal. An advantage of existing scintillators is their large detection volume. These techniques are applied to the patient for several diverse projections, making it possible to swiftly collect data for positron imaging. Further description of these techniques can be found in Bishop, U.S. Pat. No. 6,671,541, which is hereby incorporated herein, in its entirety, by reference thereto.

The invention utilizing the technology of the condensed photomultipliers includes corresponding highly effective light guide structure to very quickly deliver data, and data processing systems to process the data. Photomultiplier tubes (PMTs) are extremely sensitive detectors of light in the ultraviolet, visible and near infrared light spectrum. PMTs multiply signals received by their detectors, which are produced by incident light, by multiply the signal up to as much as $10^8$, thereby providing enough multiplicative power for resolution of single photons. Semiconductor devices such as avalanche photodiodes may be substituted for PMT's, but PMTs are typically used.

The imaging elements of the CT machine 90 encompass a devoted, speedy, receptive, compact and cost-effective imaging gamma camera system, such as is currently available in CT scanning machines, such as available from General Electric, and other CT manufacturers. A description and diagram of scintillation detectors can be found at upei.ca/~phys221/MH/HOw_they_work_/how_they_work_.html which is hereby incorporated by reference herein in its entirety. A copy of this webpage, downloaded on Jun. 21, 2007 is also being submitted in an Information Disclosure Statement in this case, and is hereby incorporated herein, in its entirety, by reference thereto. Additionally, a diagram of the operation of a scintillation detector (scintillation crystal and photomultipliers) is shown at universe-review.ca?108-24-scintillator.jpg which is hereby incorporated by reference herein, in its entirety. A copy of this webpage, downloaded on Jun. 21, 2007 is also being submitted in an Information Disclosure Statement in this case, and is hereby incorporated herein, in its entirety, by reference thereto.

After the analysis phase the coordinate information with respect to the location of surgical target area(s) (e.g., weak arteries or veins, or other body conduits or organs in need of repair) will be stored in the main computer's memory of system 100. This coordinate information will be reviewed by the decision-makers, e.g., doctors, material scientists, computer operators, etc., as to how severe the arteries' defects are. They will then analyze and diagram the proposed solution.

The decision-makers map out, that is, diagram the surgical target area regions in need of repair. This diagram (computer program) is used to instruct or guide the Nuclear Magnetic Resonance (NMR) control system 80 of system 100 to navigate and direct delivery of the one or more devices to one or more surgical target locations in need of repair and located by specific coordinates on the map. The decision-makers determine the size and shape or configuration of each device 10 needed and where to position each one for implantation. Each device 10 is provided with a unique identification number, and the Nuclear Magnetic Resonance (NMR) control system 80 uses these unique identification numbers to guide the devices 10 to the target locations.

The CT/MRI machine 90 functions as a surgical target analysis and repair management sub-section of system 100 and is configured to analyze all types of artery, vein or other vessel surfaces for defects. The purpose of these assessments is to make the determination of repair preparation requirements and to provide the best possible reconstruction quality examination of the vessel's surface to be repaired. The analysis and repair management sub-section (CT/MRI machine 90) can identify the number and thickness of each layer in a multi-layer vessel arrangement. Analysis by CT/MRI machine 90 can facilitate the determination of the location and quality of vessel walls, as well as the depth of the wall and the thickness and other dimensions of a device 10 needed to provide ample reinforcement of a defect in a vessel wall.

As noted above, each cell 20 can be provided with positive top, negative bottom, negative left, and positive right charges on the polarity sections 32. This polarity allows the cells 20 to conjoin concurrently. Each cell 20 may have multiple states such as: strong polarity (collapsed state); weak polarity (expanded state); and no polarity (neutral state), for example. In the neutral state, the cells 20 are not attracted to each other, and can thus float freely and independently. IN order to move the cells 20 closer together, the polarity (magnetic attractive forces) is increased. In order to move the cells further apart but maintain the integrity of the device 10, the polarity is decreased, although still maintained above neutral. Polarity and relative degrees of polarity (attraction strength) is controlled by the RF signals sent to the cells 20 via NMR machine 80.

As noted above, each cell has an RED code area for cell RFID 22c, patch RFID 22p and other communication control information programmed with it. The bio-compatible semiconductor cell 20 and patch 10 may contain a small "tracer" apportionment of radioactive material, and this material is not threatening to the individual undergoing the operation. This characteristic (radioactive element), combined with the RFID capability, permits the master NMR 80 to assimilate the accurate location of the patches 10 at all times. The master NMR machine may be controlling multiple patches at the same time within the body; the combination of the RFID information and the radioactive tracer permits the command of multiple patches 10 at the same lime.

After a device 10 is assembled using individual cells 20, the device 10 is programmed with respect to the corner positioning cells 20, upper right, upper left, lower right, lower left, etc., to be arrangement cells. This is done through the communication area 22 of the bio cells 20 in conjunction with the unique REID of the appropriate cells and patches. The corner positioning cells of each patch are critical with respect to the NMR guiding the patch (stent) to the area in need of repair. The bio-compatible semiconductor cells 20 and patch 10 will accommodate a small "trace" portion of radioactive substance, and is not dangerous to the person undergoing the operation. This attribute, associated with the RFID capability, permits the master NMR to realize the exact position of the patch at all times.

This positioning information is used to place the patch 10 over the area of the vessel in need of repair under the guidance of the NMR technology. The algorithms programmed into the controlling computer determine the sequence of guiding each patch to the appropriate location. With each patch having a unique RFID and trace radioactive element, the controlling computer will be able to track and position multiple patches at the same time. By use of the polarity sections (four) of each cell, the patch dimensions can be changed at any time. Utilizing the link and polarity switches of each patch cell permit this characteristic.

Fusing a Device to Tissue

One method of delivering a device 10 into a patient 1 includes the formation of an incision in a femoral artery, vein or other vessel in need of repair. Then one or more devices 10 are injected and controlled within the circulatory system or other vessel or duct system. Within the artery, the patches 10 are supervised by the NMR machine of system 100. The patches 10 are firmly planted within the vessel in need of repair using the NMR system. Device 10 typically has length and width dimensions greater than those of a defect to be repaired, so that device 10 extends lengthwise and widthwise over the defect to interface with healthy tissues surrounding the defect.

Device 10 is moved through the vessel, coordinate data previously taken by the CAT system 90, to the area of the weak vessel wall. Based on the detailed three-dimensional map of the pertinent cardiovascular vessels and the surgical target area provided by CT machine 90 and to which NMR machine 80 has been registered, NMR machine 80 provides magnetic energy fields, together with the RECD code of a device 10 to drive device 10 though the vascular system to deliver it to the surgical target location. When the device 10 is in the proper location (i.e. adjacent the target surgical location where it is to be fused to the wall of the vessel), through computer control, the stent 10 can be expanded to its expanded configuration, from its collapsed configuration, which it is in during insertion into the body and delivery through the vessel(s). That is, device 10 can be opened (expanded) from its collapsed state, if necessary, to the correct size required. Communications with each of the patch cells 20 allow this procedure.

Device 10 is then contacted to and fused to the vessel wall by use of radio frequency fusion energy provided by NMR machine 80. This fusion process is much simpler and less risky than current fixation techniques. The radio frequency is such that the energy does little or no harm to the human body. The radio frequency energy does effect the fusion material on each cell though, as the fusion area heats up, it fuses to the vessel wall. Also, when the fusion process is taking place, that is, the radio frequency fusion energy is sent to the fusion area of the cell, the communication area and link sections may be destroyed. This fact is not critical because these areas are not needed any more; they have already completed their function.

Accordingly, the present methods and devices do not require anchoring rods, anchoring pins, staples, helical springs or coils on the devices 10 or vessels, thereby greatly reducing the risk of rupturing a vessel, which can result in serious injury or death to the patient.

Each device 10 size can be determined, based on analysis of the CT scan from the CT system 90. As noted above, the fusion areas of device 10 can be energized by signals from the NMR system 80 to heat them up to cause fusion to tissue at the surgical target area (e.g., artery or vein or other conduit or organ). After the fusion process is completed and in place, hemodynamic tension will assure a continued fluid firm seal between the device 10 and the healthy vessel wall tissue.

Energy transmitted to the fusion portions 26 of the cells 20 of device 10 (e.g., patch/stent/graft) does not have any substantial negative effect on the body as the energy (RF radiation) from the NMR sub-section 80 is transported through the healthy body tissue. This energy (radiation) is received by the fusion portions 26 of the biocompatible cells 20 and changes the property of the cell 20 by use of this energy; the cell 20 will be allowed to coagulate and be fused to the artery or vessel wall, thus, sealing the weak portion of the vessel.

Device 10 is held against the wall of the vessel by the magnetic properties of the patch positioning material 24 driven by the magnetic field applied by NMR sub-section 80. Device 10 is sealed to the vessel wall along its perimeter.

Compliance matching of device 10 to have a similar compliance to the compliance of the wall of the vessel to which it is to be fused is important for the long term success of the functioning of device 10 as a small diameter vascular graft prosthesis. Without compliance, turbulence can develop at the boundaries between device 10 and the vessel wall. A ridge of flexible material (not shown) may be provided to act as a buffer between the fusion material and the vessel wall.

Figure 7:
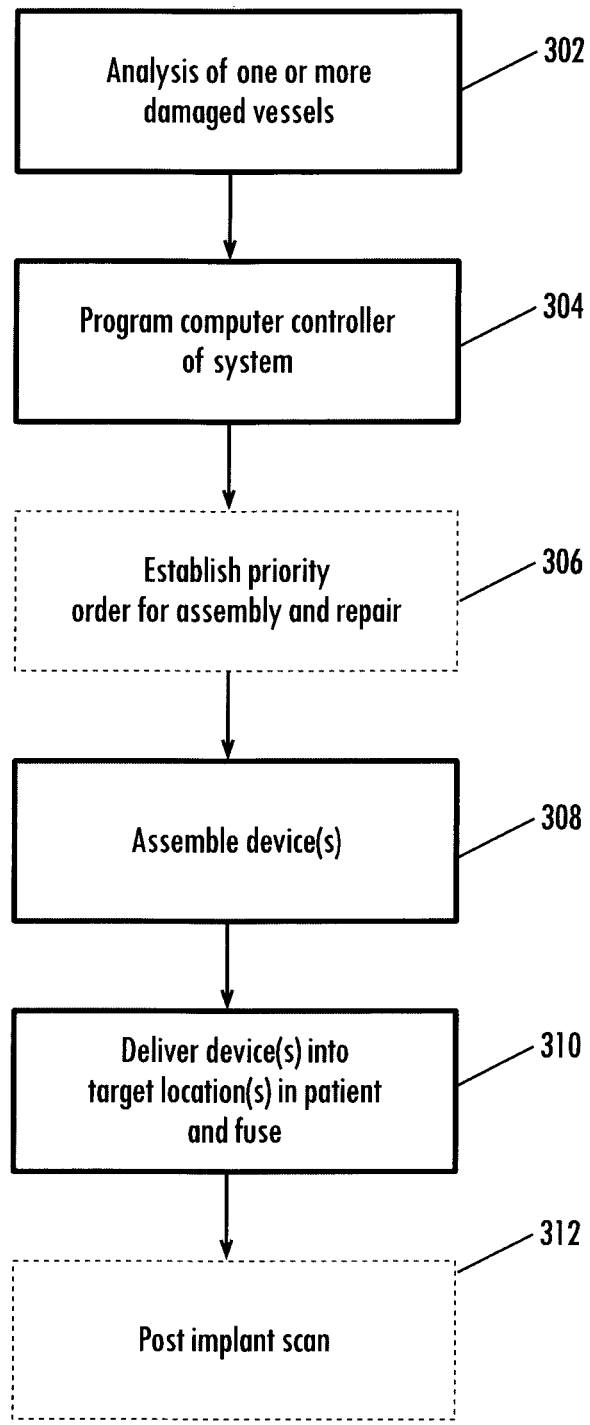
FIG. 7 illustrates events that may be carried out for treatment of a damaged vessel according to a method embodiment of the present invention.

Referring now to FIG. 7 events that may be carried out for treatment of a damaged vessel according to a method embodiment of the present invention are shown. At event 302, analysis of one or more damaged vessels is performed, in order to ascertain, for example, location coordinates of one or more damaged areas, as well as dimensions of the one or more damaged areas as information that will be used in the assembly of one or more devices and in the guidance, delivery and implantation of the one or more devices 10. Thus, diagnosis of one or more vessels is performed to determine the location(s) of an aneurysm(s) or other fault(s). This analysis can be performed, for example, by performing a CAT scan of the patient 1, using the CAT scan sub-section 90 of system 100. The exact coordinates of the damaged portion(s) of the artery(ies) or vein(s) or other vessel(s) in need of repair are determined, in order to provide a map thereof for reference thereto by NRM sub-section 80 during performance of the delivery and implantation of the device(s) 10.

As noted, examination of the artery(ies), vein(s) or other vessel area to be repaired is determined using the CAT or MRI section 90 of system 100. Any of Computerized Axial Tomography (CAT), Magnetic Resonance Imaging (MRI), Fluoroscopic or X-ray techniques, or any combination thereof, may be used to scan the circulatory system or other ducts or vessels in the patient, for weak arteries, veins or other vessels, or other defects, such as blockages or partial blockages, etc.

After scanning the patient for defects (the scan may be directed primarily to one area or vessel thought to be defective, one system, such as the circulatory system, urinary ducts, etc., or one organ, such as the brain, lungs, heart, etc., or may be a general body scan to look everywhere), the computer controller of system 100 is next programmed (such as via console 95, for example) at event 304 with information needed to perform implantation of one or more devices 10 into the patient 1 to repair one or more vessel defects. Information about the size(s) of the defect(s) can also be inputted to be used by device assembly sub-section 210 so that device(s) 10 of the appropriate dimensions can be automatically assembled from cells 20. The coordinates and locations of the defect(s) in the vessel(s) to be repaired are inputted, relative to the map generated by the scan. With this computer controlled surgery process, the coordinate information is programmed into the computer to determine the exact size of each stent 10 to be used, and allow optimum control and placement of the patches (stents) 10 covering the surfaces to be repaired.

Optionally, a surgeon or medical team may establish a priority of damaged arteries or veins or other vessels to be repaired, at event 306, and an algorithm used by the controlling computer can use the priority list to ascertain a sequence in which the devices 10 are assembled and the priority regarding the order of deployment of the devices 10 into the vessels in need of repair. If there is only one device 10 to be assembled and implanted or if there is no particular criticality in the order in which a multiplicity of devices 10 are assembled and implanted, then optional event 306 need not be carried out. In the case of only one device 10, this is straightforward, as the single device is then assembled and implanted. In the case of multiple devices 10, system 100 may assemble and implant these devices 10 in an order of first in, first out, or there may be some other default algorithm by which to automatically set priorities using a rule-based algorithm. As one example, one rule may be that if two or more devices 10 are to be implanted in the same vessel, then the device to be implanted at the location most distal along the vessel, from the location of implantation into the patient 1 will be inserted and implanted first, followed by the device to be implanted in the next most distal location, and so forth. Many other rules may be implanted in conjunction with, or in lieu of this example.

At event 308, the one or more devices 10 to be implanted are assembled in the assembly sub-section 210 in a manner as described above, using any information having been inputted with regard to size of devices 10 needed, as well as priority of assembly.

Next, at event 310, the one or more devices 10 are delivered into the patient 1 and into the vessels or ducts in need of repair, and fused to the vessels or ducts in the target surgical locations identified by the previous scanning event and programming of the coordinates of these defects. Delivery and guidance of device(s) 10 are performed by NMR subsection 80, having been registered to a map of the patient 1 provided by the CAT sub-section 90, so that landmarks of the anatomy sensed by the NMR system 80 have the same coordinates as those same landmarks on the map from the CAT scan. Accordingly, NMR sub-section 80 can then be controlled by the computer controller to generate magnetic fields to navigate each device 10 through the tortuous anatomy of the vessels, ducts or other structures that device(s) is/are to be implanted in. When the exact target locations of a defect have been reached by a device 10, NMR system can then direct the device to cover the defect (optionally, after having expanded the device 10 to the expanded configuration), seal the perimeter of the device 10 against healthy tissue surrounding the defect, and then deliver RF energy to the fusion portions 26 of the cells to fuse device 10 to the vessel or duct, thereby repairing the defect. When multiple devices 10 are being implanted, delivery, guidance and fusion steps may be carried out serially, one device at a time, or may be carried out in parallel, thereby reducing the time of the overall surgery, by generating more than one magnetic field at a time, each with the patch RFID of the device to be controlled by that particular magnetic field.

After fusing a device, a scan (e.g., CAT Scan or other visualization) of the target surgical area may be performed to confirm that the device 10 has been successfully implanted. Additionally, a scan may be performed after initially sealing the perimeter of the device 10 and prior to performing fusion, to ensure that device 10 is properly fixed prior to fusing. After performance of all implantations, a post-implant scan may optionally be performed at event 312 to confirm successful completion of the procedures, or to inform the operator if one or more devices 10 need to be removed or replaced.

Through the use of Nuclear Magnetic Resonance (NMR) techniques to deliver, position and fuse device 10 are used to position the graft (cell-fabricated patch or graft) during assembly of the patches and during the surgery. With this procedure, patients can be treated at a reduced expense, by less experienced surgeons/technicians, in a larger number of facilities, in less time, with a greater survival rate, and less invasively than most current practices. Devices 10 are also very low profile and congruent with the tissue walls of the vessel, thereby diminishing the danger of valve occlusions by thrombus, thromboembolism and anti-coagulant associated hemorrhage, as it is known that, for antithrombogenity, it is important to have a low peak-to-valley height (ruggedness) in order to avert the deposition and destruction of corpuscular contents of the blood and the cause of the coagulation system connected therewith. It is also understood that uninterrupted charge exchanges between coagulation-specific proteins and the implant surface should be prohibited.

Many of the patients who require treatment of an aortic aneurysm have other medical predicaments which are much less likely to be intensified by a operation which takes a small measure of time and which does not surgically infringe on the abdominal cavity. Tissues should begin to grow into the graft within two to four weeks with tissue thoroughly covering the interior side of the graft within six months, so that no fragment of the graft thereafter will interact with the blood circulating in the vessel, which will constitute a complete repair of the aneurysm.

Figure 8:
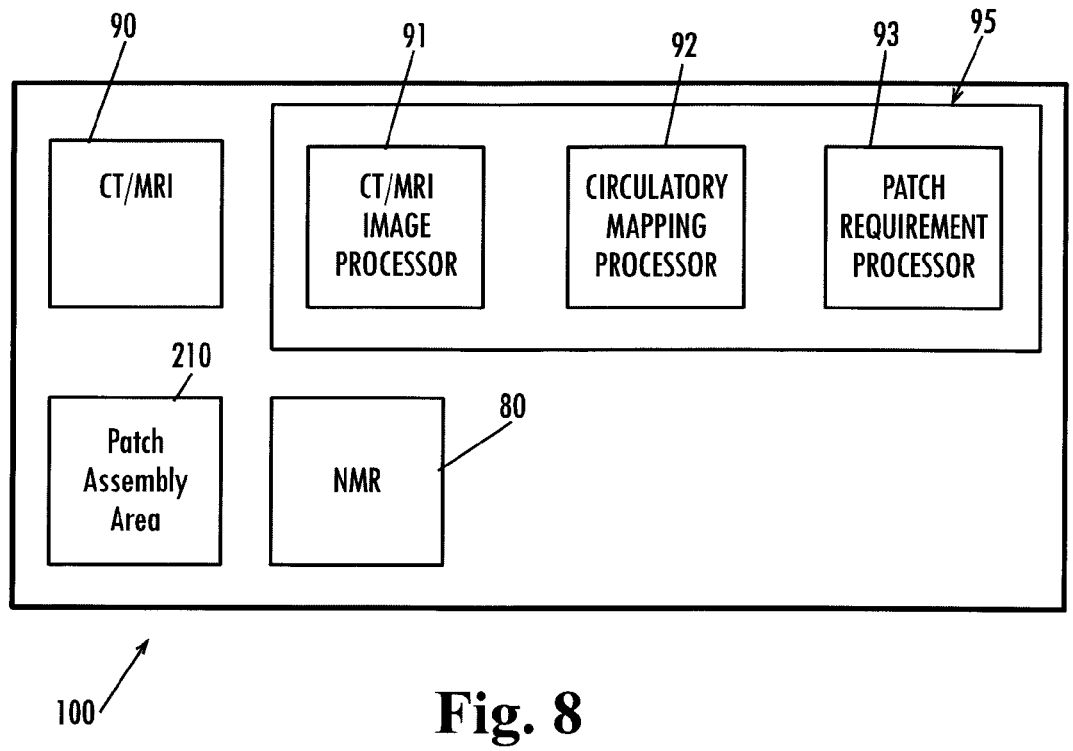
FIG. 8 is a schematic block representation of subsystems that may be included in a system according to the present invention.

FIG. 8 schematically illustrates subsystems that are included in system 100. CT/MRI 90 and NMR 80 subsystems have already been discussed above and are also shown in FIG. 1. Patch assembly area 210 was described above with regard to FIG. 4. Console 95, or portions of the CT/MRI subsystem may include processors 91, 92 and 93 for CT/MRI image processing, mapping of the patient anatomy, and patch device 10 requirements processing, respectively. Alternatively, these functions may be carried out by more or fewer processors running dedicated algorithms for the particular functions.

Figure 9:
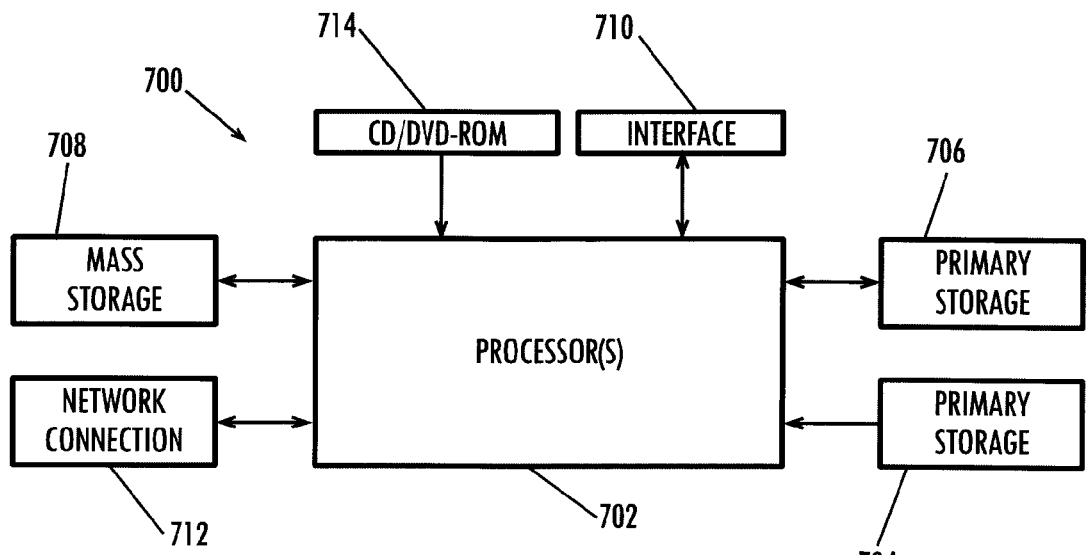
FIG. 9 illustrates a typical computer system, components of which or all of which may be employed in a system according to the present invention.

FIG. 9 illustrates a typical computer system, components of which, or all of which may be employed in system 100. The computer system 700 includes any number of processors 702 (also referred to as central processing units, or CPUs, and, for example, which may be employed in the computer controller of system 100, as well as one or more sub-sections described) that are coupled to storage devices including primary storage 706 (typically a random access memory, or RAM), primary storage 704 (typically a read only memory, or ROM). As is well known in the art, primary storage 704 acts to transfer data and instructions uni-directionally to the CPU and primary storage 706 is used typically to transfer data and instructions in a bi-directional manner Both of these primary storage devices may include any suitable computer-readable media such as those described above. A mass storage device 708 is also coupled bi-directionally to CPU 702 and provides additional data storage capacity and may include any of the computer-readable media described above. Mass storage device 708 may be used to store programs, data and the like and is typically a secondary storage medium such as a hard disk that is slower than primary storage. It will be appreciated that the information retained within the mass storage device 708, may, in appropriate cases, be incorporated in standard fashion as part of primary storage 706 as virtual memory. A specific mass storage device such as a CD-ROM or DVD-ROM 714 may also pass data uni-directionally to the CPU.

CPU 702 is also coupled to an interface 710 that includes one or more input/output devices such as video monitors, track balls, mice, keyboards, microphones, touch-sensitive displays, transducer card readers, magnetic or paper tape readers, tablets, styluses, voice or handwriting recognizers, or other well-known input devices such as, of course, other computers, any of which may be included in console 95, for example. Finally, CPU 702 optionally may be coupled to a computer or telecommunications network using a network connection as shown generally at 712. With such a network connection, it is contemplated that the CPU might receive information from the network, or might output information to the network in the course of performing the above-described method steps. The above-described devices and materials will be familiar to those of skill in the computer hardware and software arts.

The hardware elements described above may implement the instructions of multiple software modules for performing the operations of this invention. For example, instructions/ algorithms for assembling devices 10 from cells 20 may be stored on mass storage device 708 or 714 and executed on CPU 702 in conjunction with primary memory 706. Likewise, algorithms and instructions for delivery, guidance and implantation of devices may be stored on mass storage device 708 or 714 and executed on CPU 702 in conjunction with primary memory 706.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A method of implanting a device in a vessel or duct of a patient, said method comprising the steps of:
scanning the patient to provide a map of a target surgical location of a defect in the vessel or duct;
programming coordinates of the target surgical location relative to the map in a computer controller;
inserting the device through a small opening in the patient, so that no portion of the device extends out of the patient and the device is not connected to anything that extends out of the patient;
wherein the device comprises a plurality of semiconductor cells held in assembly primarily by magnetic attraction forces;
moving and guiding the device through an anatomy of the patient to the target surgical location, wherein guiding is performed by registering a device mover with the map to facilitate navigation of the device through the anatomy and to the target surgical location; and
fixing the device to the target surgical location.

2. The method of claim 1, wherein said moving and guiding are performed by a nuclear magnetic resonance machine, controlled by the computer controller and registered to the map to provide magnetic fields to move the device through the anatomy according to coordinates referenced to the map.

3. The method of claim 1, wherein said scanning is performed by a CAT scanner.

4. The method of claim 1, wherein said fixing comprises fusing at least a portion of the device to a tissue of the vessel or duct wall.

5. The method of claim 1, further comprising assembling the device from a plurality of cells, wherein said plurality of cells are guided, by a nuclear resonance machine, into position for assembly.

6. The method of claim 5, wherein the plurality of cells are assembled by polarizing portions thereof to attract to one another.

7. The method of claim 5, wherein the device is assembled to have a size determined to cover the defect, as determined by the coordinates of a location of a defect dimension.

8. A minimally invasive method of implanting a device in a patient, said minimally invasive method comprising the steps of:
scanning the patient to provide a map of a target surgical location in the patient;
programming coordinates of the target surgical location relative to the map in a computer controller;
inserting the device through a small opening in the patient, so that no portion of the device extends out of the patient;
wherein the device comprises a plurality of semiconductor cells held in assembly primarily by magnetic attraction forces;

moving and guiding the device through an anatomy of the patient to the target surgical location, wherein guiding is performed by registering a device mover with the map to facilitate navigation of the device through the anatomy and to the target surgical location; and fixing the device to the target surgical location.

9. The method of claim 8, wherein said moving and guiding are performed by a nuclear magnetic resonance machine, controlled by the computer controller and registered to the map to provide magnetic fields to move the device through the anatomy according to coordinates referenced to the map.

10. The method of claim 8, further comprising assembling the device from a plurality of cells.

11. The method of claim 10, wherein the plurality of cells are assembled by polarizing portions thereof to attract to one another.

12. The method of claim 10, wherein the device is assembled to have a size determined to cover a surgical target area at the surgical target location, as determined by coordinates of the surgical target area inputted to the computer controller.

13. The method of claim 8, wherein a plurality of devices are implanted, and at least two of said plurality of devices are implanted either serially or in parallel.

* * * * *

UNITED STATES PATENT AND TRADEMARK OFFICE
CERTIFICATE OF CORRECTION

PATENT NO.       : 9,049,988 B2
APPLICATION NO.  : 12/912383
DATED            : June 9, 2015
INVENTOR(S)      : Zurn It is certified that error appears in the above-identified patent and that said Letters Patent is hereby corrected as shown below:

In the Specification:
Column 6, line 12, please delete "be provide" and insert --be provided--;
Column 13, line 57, please delete "by apply" and insert --by applying--;
Column 15, line 35, please delete "be colored coded" and insert --be color-coded--;
Column 17, line 54, please delete "with regard to of" and insert --with regard to--; and
Column 21, line 17, please delete "IN order" and insert --In order--.

Signed and Sealed this
Twenty-sixth Day of July, 2016

Michelle K. Lee
*Director of the United States Patent and Trademark Office*